United States Patent [19]
Ogawa et al.

[11] Patent Number: 5,861,520
[45] Date of Patent: Jan. 19, 1999

[54] GLYCOLIPID ANALOGS

[75] Inventors: Seiichiro Ogawa, Tokyo; Hidetoshi Tsunoda, Chiba; Jinichi Inokuchi, Tokyo, all of Japan

[73] Assignee: Seikagaku Kogyo Kabushiki Kaisha (Seikagaku Corporation), Tokyo, Japan

[21] Appl. No.: 454,630

[22] Filed: May 31, 1995

[30] Foreign Application Priority Data

May 31, 1994 [JP] Japan .................................. 6-141187

[51] Int. Cl.$^6$ ................................ C07C 233/00
[52] U.S. Cl. .................. 554/42; 554/51; 554/55; 554/61; 554/65; 514/613; 514/625
[58] Field of Search ................ 554/61, 42, 57, 554/83, 65; 514/613, 625

[56] References Cited

U.S. PATENT DOCUMENTS 5,095,119  3/1992  Ocain et al. ...................... 548/302

OTHER PUBLICATIONS

Ogawa et al., "Synthesis of Glucosylceramide Analogues", *J. Chem. Soc., Chem. Commun.*, vol. 11, Jun. 1994, pp. 1317–1318.

Tsonado et al., "Synthesis of Glycosylceramide Analogs Composed of Imino–Linked Unsaturated 5a–Carbaglycosyl Residues", *Liebigs Annalen*, vol. 2, 1 Feb. 1995, pp. 279–284.

Ogawa et al., "Chemical Modification of the Sugar Moiety of Methyl Acarviosin", *Carbohydrate Research*, vol. 250, 1993, pp. 177–184.

Osieki–Newman et al, "Human acid β–glucosidase", *Biochimica et Biophysica Acta*, vol. 915, 1987 pp. 87–100.

Greenberg et al., "Human Acid β–glucoisidase", *Biochimica et Biophysica Acta*, vol. 1039, 1990 pp. 12–20.

*Primary Examiner*—Gary Geist
*Assistant Examiner*—Deborah D. Carr
*Attorney, Agent, or Firm*—Sughrue, Mion, Zinn, Macpeak & Seas, PLLC

[57] ABSTRACT

The present invention provides a compound which is a glycolipid analog having a novel structure represented by the formula (1):

$$\text{(1)}$$

wherein Z represents an imino group, an oxygen atom or a sulfur atom; m is an integer of from 3 to 12; and n is an integer of from 4 to 22; and shows a potent activity of inhibiting glycosidase and has potential physiological activities, for example, antiviral activity. The invention also provides a glycosidase inhibitor which comprises said glycolipid analog as an active ingredient.

10 Claims, 1 Drawing Sheet

GLYCOLIPID ANALOGS

FIELD OF THE INVENTION

This invention relates to glycolipid analogs constructed by artificially modifying the sugar moiety of a glycolipid. More particularly, it relates to glycolipid analogs constructed by modifying the sugar moiety of a sphingoglycolipid.

BACKGROUND OF THE INVENTION

Physiological activities of glycolipids, which are compounds widely occurring on cell membranes in vivo, have recently attracted considerable attention. On the other hand, it is expected that a sugar analog constructed by replacing an endocyclic oxygen atom of a sugar pyranose with a methylene group has various physiological activities depending on its analogy to the original sugar. Thus there have been reported that sugar analogs including sugar analogs exhibit several physiological activities of, for example, inhibiting sugar hydrolases [a) G. Hanozet, H. P. Pircher, P. Vanni, B. Oesch and G. Semenza, J. Biol. Chem., 256 (1981) 3703; b) T. Iwasawa, H. Yamamoto and M. Shibata, J. Antibiot., 23 (1970) 595; c) S. Ogawa, Y. Shibata, Y. Kosuge, K. Yasuda, T. Mizukoshi and C. Uchida, J. Chem., Soc. Chem. Comm. (1990) 1387].

The present inventors paid their attention to the sugar moiety of a glycolipid and synthesized various glycolipid analogs represented by the formula (a) through the linkage of a sugar analog to a lipid moiety via an oxygen atom, a nitrogen atom, a sulfur atom, etc. ["A study on synthesis of sugar analogs involving glycolipid analogs", Proceedings of 63rd Symposium on Organic Synthesis, 3rd to 4th Jun., 1993].

(a)

wherein X represents NH, O or S.

A glycolipid analog represented by the formula (a) is one which is analogous to a sphingoglycolipid represented by the formula (b).

(b)

wherein X represents NH, O or S.

It is known that this sphingoglycolipid closely relates to receptor functions for physiologically active substances and important cell functions, such as generation, proliferation, differentiation or immune reactions, via intercellular recognition and interactions. It is also known that this sphingoglycolipid plays a role as a receptor in the host side in the infection with bacteria or viruses.

On the other hand, it was once expected that the compound of the formula (a) might be usable as a sugar hydrolase inhibitor, in particular, a glucocerebrosidase inhibitor or an immuno-adjuvant.

However, the compound of the formula (a) has only an insufficient activity as a glucocerebrosidase inhibitor and thus it has been required to develop a compound having an improved inhibitory activity.

Regarding a β-glucocerebrosidase inhibitor, there has been reported that an N-n-alkyl-β-D-glucosylamine has a potent inhibitory effect [Biochim. Biophys. Acta, 1039, 12–20 (1990)]. However this substance has a very poor stability in an aqueous solution (half-life: 10 to 30 minutes), which makes it less usable. On the other hand, an N-n-alkyldeoxynojirimycin strongly inhibits β-glucocerebrosidase [Biochim. Biophys. Acta, 915, 87–100 (1987)]. However it is reported that this substance also inhibits glucosylceramide synthetase [J. Biol. Chem., 269 (11), 8362–8365 (1994)], which indicates that it has a low specificity.

It has been also required to develop glycolipid analogs capable of inhibiting various cerebrosidases of sugars other than glucose, for example, galactocerebrosidase.

It has been furthermore required to develop compounds each having a novel structure and potential physiological activities, such as antiviral activity or activity of improving nervous functions, as glycolipid analogs.

SUMMARY OF THE INVENTION

An object of the present invention is to provide compounds which are glycolipid analogs with a novel structure, have a high stability in the form of an aqueous solution, show an excellent inhibition specificity and a potent activity of inhibiting glycosidase and have potential physiological activities, such as antiviral activity or activity of improving nervous functions.

In order to solve the above-described problems, the present invention provides:

1) a glycolipid analog represented by the formula (1):

(1)

wherein Z represents an imino group, an oxygen atom or a sulfur atom; m is an integer of from 3 to 12; and n is an integer of from 4 to 22;

2) the glycolipid analog as described in the above 1), wherein Z represents an imino group and n is an integer of from 4 to 16;

3) the glycolipid analog as described in the above 1), which is represented by the formula (1a) or (1b):

(1a)

(1b)

wherein Z represents an imino group; X and Y are different from each other and each represents a hydrogen atom or a hydroxyl group; m is an integer of from 3 to 12; and n is an integer of from 4 to 16;

4) the glycolipid analog represented by the above formula (1) which is selected from a group consisting of (2S,3R,4E)-1-[(5a-carba-β-D-xylo-hex-5-enopyranosyl)amino]-2-(hexadecanoylamino)-4-octadecen-3-ol, (2S,3R,4Z)-1-[(5a-carba-β-D-xylo-hex-5-enopyranosyl)amino]-2-(hexadecanoyl-amino)-4-octadecen-3-ol, (2S,3R,4E)-1-[(5a-carba-α-L-arabino-hex-5-enopyranosyl)amino]-2-(hexadecanoylamino)-4-octadecen-3-ol and (2S,3R,4Z)-1-[(5a-carba-α-L-arabino-hex-5-enopyranosyl)amino]-2-(hexadecanoylamino)-4-octadecen-3-ol;

5) a glycosidase inhibitor which comprises a glycolipid analog as described in the above 1) as an active ingredient;

6) the glycosidase inhibitor as described in the above 5) which is a glycocerebrosidase inhibitor;

7) the glycosidase inhibitor as described in the above 6) which shows at least glucocerebrosidase inhibitory activity or galactocerebrosidase inhibitory activity;

8) the glycosidase inhibitor as described in the above 7) which has β-glucocerebrosidase inhibitory activity, and the active ingredient is represented by the formula (1a) or (1b):

wherein Z represents an imino group, an oxygen atom or a sulfur atom; m is an integer of from 3 to 12; n is an integer of from 4 to 22; X represents a hydrogen atom; and Y represents a hydroxyl group; and 9) the glycosidase inhibitor as described in the above 7) which has β-galactocerebrosidase inhibitory activity, and the active ingredient is represented by the formula (1a) or (1b):

wherein Z represents an imino group, an oxygen atom or a sulfur atom; m is an integer of from 3 to 12; n is an integer of from 4 to 22; X represents a hydroxyl group; and Y represents a hydrogen atom.

DETAILED DESCRIPTION OF THE INVENTION

The present invention relates to glycolipid analogs having a novel structure represented by the formula (1). Any stereoisomer falls within the scope of the present invention, so long as it satisfies the above requirement.

The glycolipid analog according to the present invention involves every glycolipid analog having the same configuration as that of a hexose as well as its geometrical isomers and stereoisomers in the lipid moiety, so long as it is constructed by replacing an endocyclic oxygen atom of a hexose pyranose with a methine group and having a double bond between C5 and C5a. The configuration of the above-described Z, which participates in the attachment of the sugar analog moiety to the lipid moiety (corresponding to a glycoside bond), to the hydroxyl group at the 6-position of the sugar analog may be either trans-form or cis-form, that is either an α-anomer or a β-anomer. From the viewpoint of the analogy to natural glycoceramide, it is preferable to select the β-anomer.

Because of having the above-described structure, the glycolipid analog of the present invention is widely applicable to various purposes through the arrangement of its stereostructure. For example, the glycolipid analog of the present invention is useful as an active ingredient of a glycosidase inhibitor. This glycosidase inhibitor is applicable to a glycosidase capable of cleaving an arbitrary glycoside bond. In particular, it is useful as a glucocerebrosidase inhibitor and/or a galactocerebrosidase inhibitor. It is possible to control the inhibitory activity of the glycolipid analog of the present invention on various glycosidases by modifying its stereostructure.

The present invention relates particularly to the glycolipid analogs represented by the formula (1a) or (1b). However, the present invention is not restricted to these compounds, as described above.

wherein X and Y are different from each other and each represents a hydrogen atom or a hydroxyl group; and Z, m and n are each as defined above.

wherein X and Y are different from each other and each represents a hydrogen atom or a hydroxyl group; and Z, m and n are each as defined above.

The glycolipid analogs represented by the formulae (1a) and (1b) correspond to a structure constructed by replacing the sugar moiety (glucose or galactose) of a natural glycolipid represented by the formula (c):

wherein X and Y are different from each other and each represents a hydrogen atom or a hydroxyl group (the lipid moiety is omitted since it is the same as the one given in the formula (1a) or (1b)); with a carbocyclic sugar analog (i.e., an O-glycoside structure) having a double bond or another structure constructed by further replacing the O-glycoside with N-glycoside (Z=NH) or S-glycoside (Z=S).

That is to say, when X is H and Y is OH in the formula (c), this glycolipid is a glucosylceramide compound. When X is OH and Y is H, it is a galactosylceramide compound.

When X is H and Y is OH in the formulae (1a) and (1b), the compound is a glycolipid analog of a glycosylceramide compound. When X is OH and Y is H, it is a glycolipid analog of a galactosylceramide compound. Regarding the double bond in the lipid moiety, the glycolipid analogs of the formulae (1a) and (1b) have trans- and cis-configurations, respectively.

When the compounds of the formulae (1a) and (1b) are glycolipid analogs of a glucosylceramide compound, they strongly and specifically inhibit β-glucocerebrosidase. When these compounds are glycolipid analogs of a galactosylceramide compound, they strongly and specifically inhibit β-galactocerebrosidase.

In the formulae (1), (1a) and (1b), it is preferable that Z is NH, m ranges from 3 to 12, and n ranges from 4 to 22, with n ranging from 4 to 16 more preferably.

Although the glycolipid analog of the present invention may be produced by any method without restriction, it is preferably synthesized in accordance with the following method.

The glycolipid analog of the present invention can be fundamentally obtained by synthesizing a sugar analog moiety having an optionally protected hydroxyl group and a sphingosine moiety having optionally protected amino and hydroxyl groups, linking these moieties to each other via Z, deprotecting the compound thus obtained, and attaching a fatty acid to the amino group in the lipid moiety via an amide bond. The synthesis of the glycolipid analog will be described in detail below.

1. Synthesis of compound of formula (2) [$R_1$=a protecting group, $R_2$=H] and another compound of formula (2) [$R_1$=H, $R_2$=protecting group]:

wherein $R_1$ represents a hydrogen atom or a protecting group for a hydroxyl group [for example, benzoyl(Bz), p-nitrobenzoyl, naphthoyl] and $R_2$ represents a hydrogen atom or a protecting group for a hydroxyl group [for example, silyl such as t-butyldimethylsilyl (t-BDMS), diethyltrimethylsilyl, t-butyldiphenylsilyl].

A compound of the formula (2) wherein $R_1$ and $R_2$ each represents a hydrogen atom is dissolved in a basic solvent such as α-picoline, γ-picoline or piperidine. Then a reactive derivative having a protecting group $R_1$ such as a halide (for example, benzoyl chloride, p-nitrobenzoyl chloride, naphthoyl chloride) is added thereto in an equivalent amount or more, preferably 1 to 2 equivalent amount, more preferably 1 to 1.2 equivalent amount, at a temperature of −20° to 20° C. Then the mixture is reacted for a definite period of time, for example, for 1 to 24 hours under stirring to thereby replace the hydrogen atom with the protecting group $R^1$ and the obtained product is separated by chromatography. Next, the product thus obtained is dissolved in an organic solvent such as N,N'-dimethylformamide (DMF) and a reactive derivative having a protecting group $R_2$ (for example, t-butyldimethylchlorosilane) is added in an equivalent amount or more. Then the mixture is reacted for a definite period of time, for example, for 6 to 48 hours, under stirring to thereby deprotect $R_1$ and protect $R_2$. After concentrating and purifying the reaction mixture, the title compound is obtained.

2. Synthesis of compound of formula (3)

wherein $R_2$ represents the above-mentioned protecting group; and $R_3$ represents a protecting group for an amino group [for example, dinitrophenyl (DNP), acetyl, trifluoroacetyl, benzoyl, p-nitrobenzoyl, methylsulfonyl, p-toluenesulfonyl, trifluoromethanesulfonyl].

The compound of the formula (2) ($R_1$=H, $R_2$=protecting group) obtained in the above 1) is dissolved in an organic solvent and a reducing agent such as triphenylphosphine is added thereto in an equivalent amount or more, preferably 1 to 1.5 equivalent amount, in an inert gas atmosphere. Then the reaction mixture is stirred for a definite period of time, for example, for 10 minutes to 4 hours, at 40° to 80° C. and concentrated under reduced pressure. The residue is dissolved and a reactive derivative having a protecting group $R_3$ (for example, 2,4-dinitrofluorobenzene, acetyl chloride) is added thereto in 1 to 3 equivalent amount, preferably 1 to 1.5 equivalent amount. After stirring and purifying by chromatography, the compound of the formula (3) and the compound of the following formula (4) are obtained.

wherein $R_2$ and $R_3$ are each as defined in the formula (3).

The terminal hydroxyl group of the compound of the formula (4) is replaced with iodine and then the resulting compound is reacted in the presence of an equivalent amount or more, preferably 1 to 2 equivalent amount, of silver fluoride, zinc dust or the like at a temperature of from 0° C. to room temperature for 1 to 12 hours under stirring. Thus the compound of the formula (3) can be obtained.

3. Synthesis of compound of formula (6)

wherein $R_2$ and $R_3$ are each as defined in formula (3); $R_4$, $R_5$, $R_6$ and $R_7$ each represents a protecting group for a single hydroxyl group, or two arbitrarily selected from them (preferably those adjacent to each other) form a protecting group for a hydroxyl group together, or a hydrogen atom; and Z is as defined above.

A compound represented by the formula (5):

wherein $R_4$, $R_5$, $R_6$ and $R_7$ are each as defined above; and $R_8$ is a functional group containing N, O or S atom (for example, amino, alkylamino, hydroxyl, thioacetyl, sulfonamide); and a compound represented by the formula (3) are dissolved in an organic solvent [for example, 2-propanol, methanol, ethanol, n-propanol, n-butanol, iso-butanol, tert-butanol, dimethylformamide (DMF), dimethyl sulfoxide (DMSO)] and reacted under stirring at a temperature of 50° to 180° C., preferably 100° to 130° C., for 1 to 10 days, preferably 2 to 6 days. Then the reaction mixture is concentrated under reduced pressure and the residue thus obtained is purified by chromatography, preferably silica gel chromatography with the use of, for example, Silica Gel 40, 60 (manufactured by Merck & Co., Inc.), Wacogel C-200, C-300 (manufactured by Wako Pure Chemical Industries, Ltd.) or K-60 (manufactured by Katayama Kagaku K. K.) as a carrier and a mixture of ethyl acetate with toluene as an eluent. Thus the compound of the formula (6) can be obtained.

Examples of the protecting groups ($R_4$ to $R_7$) in the formula (5) include t-BDMS, methoxymethyl (MOM), 2-methoxyethoxymethyl, mesyl, tosyl, benzoyl, benzylidene, isopropylidene, cyclohexylidene and cyclopentylidene groups. Among these protecting groups, divalent ones (for example, benzylidene, isopropylidene, cyclohexylidene, cyclopentylidene) are those which have been formed by a combination of two groups arbitrarily selected from among $R_4$ to $R_7$. When the substituent corresponding to the position of $R_5O$ forms an equatorial bond, preferable examples of the protecting groups include those formed by a combination of $R_4$ with $R_5$ or $R_6$ with $R_7$ (for example, isopropylidene, cyclohexylidene, cyclopentylidene, benzylidene). It is also possible that $R_4$ and $R_5$ form a benzylidene group, a cyclohexylidene group, etc. together while $R_6$ is an MOM group, a 2-methoxyethoxymethyl group, etc. and $R_7$ is an MOM group, a 2-methoxyethoxymethyl group, etc. When $R_5O$ forms an axial bond, on the other hand, it is preferable that $R_4$ is a t-BDMS group, $R_5$ is a hydrogen atom or an acetyl group, $R_6$ is an MOM group, a 2-methoxyethoxymethyl group etc. and $R_7$ is an MOM group, a 2-methoxyethoxymethyl group etc.

A compound wherein $R_5O$ is a hydroxyl group (i.e., $R_5$ is a hydrogen atom) and forms an axial bond may be obtained in the following manner. A compound wherein $R_5O$ is a hydroxyl group and forms an equatorial bond, $R_4$, $R_6$ and $R_7$ are protecting groups and $R_8$ is a group from which Z can be derived (for example, azide) is dissolved in an organic solvent such as methylene chloride, dichloroethane or chloroform. In the presence of a molecular sieves powder [made of crystalline zeolite (silicate), pore size: 3 to 10], an oxidizing agent such as pyridinium chlorochromate (PCC) or chromium trioxide is added thereto in 1 to 5 equivalent amount, preferably 2 to 4 equivalent amount. After stirring for 30 to 120 hours at room temperature, the obtained product is purified by using, for example, a silica gel column (eluent: ether). Thus a ketone compound represented by the following formula (7) is obtained.

The thus-obtained ketone represented by the formula (7) is dissolved in, for example, a toluene solution of a reducing agent [for example, 1M-diisopropyl aluminum hydride (DIBAL-H)] is added thereto at −78° C. to 20° C. and the mixture was stirred for 5 minutes to 1 hour, preferably 10 to 30 minutes. Then the ketone is subjected to reduction to thereby invert the conformation of $R_5O$. Next, an alkali solution (for example, a 5% solution of sodium hydroxide) is added to the reaction mixture followed by the extraction with an organic solvent such as ethyl acetate. After washing, drying and purifying by, for example, chromatography, a compound, wherein $R_4$, $R_6$, $R_7$ and $R_8$ are each the same as the one before the reaction and $R_5O$ is a hydroxyl group forming an axial bond, can be obtained. If necessary, $R_8$ may be converted into another functional group such as an amino group or a hydroxyl group.

4. Synthesis of compound of formula (8)

wherein $R_3$, Z and m are each as defined above.

The protecting groups (other than $R_3$) in the compound represented by the formula (6) are deprotected to thereby give a compound represented by the formula (8). The deprotecting conditions may be selected over a wide range depending on the type of Z.

More particularly, the compound represented by the formula (6) is dissolved in an organic solvent such as tetrahydrofuran (THF). Then a deprotecting agent such as tetrabutylammonium fluoride (nBu$_4$NF) or boron trifluoride etherate is added thereto in an equivalent amount, preferably 1 to 2 equivalent amount and the mixture was reacted for 5 minutes to 1 hour, preferably 10 to 30 minutes. The reaction mixture is diluted with an organic solvent such as ethyl acetate and washed with water. The organic layer is dried over, for example, Glauber's salt or anhydrous magnesium sulfate and concentrated under reduced pressure. The resulting product is purified preferably by silica gel column chromatography using eluent, such as ethanol:toluene=1:7 or methanol:chloroform=1:5, to thereby give the compound of the formula (8). 5. Synthesis of compound represented by formula (1)

The compound represented by the formula (8) is dissolved in an organic solvent, preferably a solvent mixture of acetone, methanol and water (3:5:2). Then a basic resin, preferably Amberlite IRA-400 (OH$^-$) is added thereto at room temperature. After stirring, the reaction mixture is filtered and the filtrate is concentrated under reduced pressure. The resulting residue is dissolved in an organic solvent. Then a halide (preferably chloride) of a fatty acid corresponding to the fatty acid moiety (n is as defined above) of the compound of the formula (1) and an aqueous solution of sodium acetate are added thereto in 1 to 2 equivalent amount at room temperature. Then the mixture is stirred for 5 minutes to 1 hour, preferably 10 to 30 minutes, and thus the protecting group $R_3$ is deprotected and the fatty acid halide is attached to the amino group via an amide bond. The reaction mixture is diluted with an organic solvent (preferably THF, etc.) and washed with a saturated aqueous solution of sodium chloride. Then the organic layer is dried over a dehydrating agent such as anhydrous magnesium sulfate and, if necessary, concentrated under reduced pressure. After purifying, the glycolipid analog of the present invention represented by the formula (1) is obtained.

The compound of the present invention represented by the formula (1) involves arbitrary stereoisomers thereof. A compound having a desired stereostructure can be synthesized fundamentally by applying the above-mentioned method.

For example, compounds represented by the formulae (1a) and (1b) can be each synthesized by using a compound represented by the formula (5-1) or (5-2) in place of the above-mentioned compound of the formula (5), a compound represented by the formula (4-1) or (4-2) (in which the same structure as that of formula (4) is omitted) in place of the above-mentioned compound of the formula (4), and a halide of a fatty acid corresponding to the acyl group (n=4 to 22) in the formula (1a) or (1b).

wherein $R_4$ to $R_8$ are each as defined in the formula (5), and preferably $R_4$ and $R_5$ or $R_6$ and $R_7$ form together a protecting group for a hydroxyl group such as an isopropylidene group.

wherein $R_4$ to $R_8$ are each as defined in the formula (5), and preferably $R_4$ is t-BDMS, $R_5$ is a hydrogen atom and $R_6$ and $R_7$ are each an MOM group.

wherein $R_2$ and m are each as defined above.

wherein $R_2$ and m are each as defined above.

The glycolipid analog of the present invention can be formulated into a dosage form with a pharmaceutically acceptable carrier.

A preparation to be administered orally or parenterally can be obtained by using the glycolipid analog with a carrier, an excipient and other additives.

As an oral preparation, there may be mentioned a solid preparation such as a powder, a granule, a capsule, a tablet, etc.; and a liquid preparation such as a syrup, an elixir, an emulsion, etc. The powder can be obtained by, for example, mixing with an excipient such as lactose, starch, crystalline cellulose, calcium lactate, calcium hydrogen phosphate, magnesium aluminate metasilicate, silicic anhydride, etc. The granule can be obtained by adding the above excipient and, if necessary, for example, a binder such as saccharose, hydroxypropyl cellulose, polyvinyl pyrrolidone, etc. or a disintegrator such as carboxymethyl cellulose, calcium carboxymethyl cellulose, etc. and granulating the mixture by a wet method or a dry method. The tablet can be obtained by tableting the above powder or granule as such or with a lubricant such as magnesium stearate, talc. etc. Further, the above tablet or granule can be made an enteric or sustained preparation by covering it with an enteric base such as hydroxypropylmethyl cellulose phthalate, a methyl methacrylate copolymer, etc. or covering it with ethyl cellulose, carnauba wax, hardened oil, etc.

A hard capsule can be obtained by filling a hard capsule with the above powder or granule. Further, a soft capsule can be obtained by dissolving the glycolipid analog of the present invention in glycerin, polyethylene glycol, sesame oil, olive oil, etc. and covering the mixture with a gelatin film. The syrup can be obtained by dissolving a sweetener such as saccharose, sorbitol glycerin, etc. and the glycolipid analog of the present invention in water. In addition to the sweetener and water, essential oil, ethanol, etc. may be added to prepare an elixir, or gum arabic, tragacanth, polysorbate 80, sodium carboxymethyl cellulose, etc. may be added to prepare an emulsion or a suspension. Further, a flavor, a coloring agent, a preservative, etc. may be added to these liquid preparations, if necessary.

As an parenteral preparation, there may be mentioned an injection, an intrarectal administration agent, a pessary, an endermic agent, an inhalation, an aerosol, an ophthalmic solution, etc. The injection can be obtained by adding a pH-adjusting agent such as hydrochloric acid, sodium hydroxide, lactic acid, sodium lactate, sodium monohydrogen phosphate, sodium dihydrogen phosphate, etc.; an isotonicity-imparting agent such as sodium chloride, glucose, etc.; and distilled water for injection to the glycolipid analog of the present invention, sterilizing and filtering the mixture and then filling an ampoule, etc. with the mixture. Further, an injection which is dissolved when it is used can be obtained by adding mannitol, dextrin, cyclodextrin, gelatin, etc. and lyophilizing the mixture under vacuum. Also, an emulsion for injection can be made by adding a emulsifier such as lecithin, polysorbate 80, polyoxyethylene hardened castor oil, etc. to the glycolipid analog of the present invention and then emulsifying the mixture in water. The intrarectal administration agent can be obtained by adding a base for a suppository such as mono-, di- or triglyceride of cacao aliphatic acid, polyethylene glycol, etc. to the glycolipid analog, then melting the mixture by heating, pouring it into a mold and cooling it, or dissolving the glycolipid analog in polyehthylene glycol, soy bean oil, etc. and then covering the mixture with a gelatin film.

The endermic agent can be obtained by adding white petrolatum, beeswax, liquid paraffin, polyethylene glycol, etc. to the glycolipid analog of the present invention, heating the mixture, if necessary, and kneading it. A tape agent can be obtained by kneading the glycolipid analog with an adhesive such as rosin, an alkyl acrylate polymer, etc. and spreading the mixture on non-woven fabric, etc. The inhalation can be obtained by, for example, dissolving or dispersing the glycolipid analog in a pharmaceutically acceptable propellant such as inert gas, etc. and filling a pressure container with the mixture.

The dose may be suitable determined depending on age, health condition, weight, etc. of a patient. An appropriate dose can be easily determined by one skilled in the art in view of the $IC_{50}$ value relative to the enzymatic activity and the anti-HIV activity as described below.

The glycolipid analogs of the present invention can be used as a glycosidase inhibitor reagent together with a biochemically acceptable carrier. The composition for the reagent may comprise, for example: 1) the glycolipid analog of the present invention; 2) an aqueous organic solvent for dissloving the glycolipid analog, such as methanol or dimethylsulfoxide; 3) a diluent, such as water, physiological saline, buffer, or culture medium; and, if required, 4) a surfactant.

Glycolipid analogs according to the present invention is useful as a glycosidase inhibitor, such as α- and β-glucosidase inhibitors, β-galactosidase inhibitor and α-mannosidase inhibitor. The following Test Example shows that enzymes decomposing cerebrosides which are glycolipids each having the original sugar as the constituting sugar (i.e., glycocerebrosidases such as glucocerebrosidase, galactocerebrosidase, etc.) can be specifically inhibited by appropriately selecting the configuration of the hydroxyl group in the sugar analog moiety. Therefore, the glycolipid analogs of the present invention is usable in biochemical studies on these glycocerebrosidases.

Further, the glycolipid analogs of the present invention specifically inhibits a glycocerebrosidase in vivo to thereby suppress the metabolism of glycolipids (for example, gangliosides) in vivo. Thus it is expected that the expression of physiological activities based on glycolipids might be artificially modified thereby. That is to say, it is known that viruses such as human immunodeficiency virus (HIV), orthomyxovirus and paramyxovirus attach to glycolipids (for example, galactocerebroside, glucocerebroside) on the cell wall of a host. It is expected that the glycolipid analogs of the present invention would show an antiviral activity via specific inhibition of the attachment of such a virus to a glycolipid on the cell membrane of a host. It is clarified that gangliosides, which play an important role in the maintenance of nervous functions, in the brain is reduced in the case of a nervous disease such as Alzheimer's disease. It is also expected that the glycolipid analogs of the present invention prevents the decrease in ganglioside in vivo and thus provides a novel means for treating various nervous diseases.

It is assumed that the sugar analog moiety of the glycolipid analogs according to the present invention has no toxicity. This is because it is a sugar analog constituting acarbose, which has been marketed as a remedy for diabetes, and occurs in nature too.

To further illustrate the present invention in greater detail, and not by way of limitation, the following Examples will be given.

EXAMPLE 1

Synthesis of (2S,3R,4E)-1-[(5a-carba-β-D-xylo-hex-5-enopyranosyl)amino]-2-(hexadecanoylamino)-4-octadecen-3-ol (compound 1E)

1-1: Synthesis of (2S,3R,4E)-2-azido-1-benzoyloxy-4-octadecen-3-ol [compound 4E: in formula (3-5E), $R_1$=benzoyl(Bz)oxy, $R_2$=H]

(2S,3R,4E)-2-azido-1,3-dihydroxy-4-octadecene [compound 3E: in the formula (3-5E), $R_1$=$R_2$=H] (479 mg, 1.47 mmol) was dissolved in 15 ml of pyridine and 188 μl (1.62 mmol) of benzoyl chloride was added thereto at −15° C. After stirring under the same conditions for 1 hour, the mixture was further stirred at room temperature for 8 hours. The resulting product was purified by silica gel column chromatography (20 g of K-60 manufactured by Katayama Kagaku, eluent; ethyl acetate:hexane=1:10). Thus 409 mg of compound 4E was obtained (yield: 65%). The properties of compound 4E were as follows.

$[\alpha]_D^{25}$=−35° (C=1.0, CHCl$_3$). $^1$H-NMR (270 MHz, CDCl$_3$) (The data are given in accordance with the indication method of Liebigs Annalen der Chemie, the same will apply hereinafter.) δ: 8.07–8.04 (m, 2H, Ph), 7.58–7.42 (m, 3H, Ph), 5.70 (dt, 1H, $J_{4,5}$=15.4 Hz, $J_{5,6a}$=$J_{5,6b}$=7.0 Hz, H-5), 5.45 (dd, 1H, $J_{3,4}$=7.3 Hz, H-4), 4.52 (dd, 1H, $J_{1a,2}$=4.0 Hz, $J_{1gem}$=11.7 Hz, H-1a), 4.31 (dd, 1H, $J_{1b,2}$=2.1 Hz, H-1b), 4.22 (dd, 1H, $J_{2,3}$=5.1 Hz, H-3), 3.45 (ddd, 1H, H-2), 2.05 (q, 2H, J=7.0 Hz, H-6a, 6b), 1.26 (s, 22H, methylene), 0.88 (t, 1H, J=7.0 Hz, methyl). Molecular formula: $C_{25}H_{39}N_3O_3$ [molecular weight (calcd.) 429.608]. Elemental analysis calcd.: C 69.90, H 9.15, N 9.78; found: C 70.05, H 9.25, N 9.60.

1-2: Synthesis of (2S,3R,4E)-2-azido-3-(t-butyldimethylsilyloxy)-4-octadecen-1-ol [compound 5E: in formula (3-5E), $R_1$=H, $R_2$=t-BDMS]

Compound 4E (409 mg, 0.952 mmol) was dissolved in 10 ml of DMF and 431 mg (2.86 mmol) of t-butyldimethylchlorosilane and 389 mg (5.71 mmol) of imidazole were added thereto. The resulting mixture was stirred at 60° C. for 20 hours. Then the reaction mixture was diluted with ethyl acetate, washed with water and concentrated under reduced pressure. The resulting residue was dissolved in a solvent mixture comprising 4 ml of methanol and 5 ml of methylene chloride. After adding 1 ml of 1 M-methanol sodium methoxide, the mixture was treated at room temperature for 2 hours. Subsequently the reaction mixture was neutralized with an acidic resin Amberlite IR-120B(H$^+$) and then the resin was filtered off. The resulting product was purified by silica gel column chromatography (20 g of K-60 manufactured by Katayama Kagaku, eluent; ethyl acetate:hexane=1:10). Thus 304 mg of compound 5E was obtained (yield: 73%). The properties of compound 5E were as follows.

$[\alpha]_D^{25}$=−42° (C=0.92, CHCl$_3$). $^1$H-NMR (270 MHz, CDCl$_3$); δ: 5.70 (dt, 1H, $J_{4,5}$=15.4 Hz, $J_{5,6a}$=$J_{5,6b}$=7.0 Hz, H-5), 5.45 (dd, 1H, $J_{3,4}$=7.3 Hz, H-4), 4.22 (dd, 1H, $J_{2,3}$=5.1 Hz, H-3), 3.73 (dd, 1H, $J_{1a,2}$=4.4 Hz, $J_{1gem}$=11.7 Hz, H-1a), 3.66 (dd, 1H, $J_{1b,2}$=6.2 Hz, H-1b), 3.40 (ddd, 1H, H-2), 2.19 (bs, 1H, OH), 2.05 (q, 2H, J=7.0 Hz, H-6a, 6b), 1.26 (s, 22H, methylene), 0.90 (s, 9H, t-butyl), 0.88 (t, 3H, methyl), 0.09 and 0.05 (2s, each 3H, methyl). Molecular formula: C$_{24}$H$_{49}$N$_3$O$_2$Si [molecular weight (calcd.) 439.762]. Elemental analysis calcd.: C 65.56, H 11.23, N 9.56; found: C 65.25, H 11.50, N 9.42.

1-3: Synthesis of (2S,3R,4E)-3-(t-butyldimethylsilyloxy)-1,2-[(2,4-dinitrophenyl)imino]-4-octadecene (compound 6E) and (2S,3R,4E)-2-[(2,4-dinitrophenyl)amino]-3-(t-butyldimethylsilyloxy)-4-octadecen-1-ol [compound 7E: in formula (7-8E), R$_3$=OH]

Compound 5E (304 mg, 0.691 mmol) was dissolved in 6 ml of toluene. Under an argon atmosphere, 200 mg (0.760 mmol) of triphenylphosphine was added thereto and the resulting mixture was stirred at 40° C. for 20 minutes and then at 80° C. for 1 hour. The reaction mixture was concentrated under reduced pressure and the residue was dissolved in 6 ml of methanol. Then 130 μl (1.04 mol) of 2,4-dinitrofluorobenzene and 193 μl (1.38 mmol) of triethylamine were added at 0° C. and the mixture was stirred under the same conditions for 30 minutes and then at room temperature for 12 hours. The resulting product was purified by silica gel column chromatography (eluent; ethyl acetate:hexane=1:20). Thus 137 mg of compound 6E (yield: 35%) and 182 mg of compound 7E (yield: 45%) were obtained. The properties of compound 6E were as follows.

$[\alpha]_D^{26}$=−162° (C=1.2, CHCl$_3$). $^1$H-NMR (270 MHz, CDCl$_3$); δ: 8.86 (d, 1H, J=2.6 Hz, Ph), 8.27 (dd, 1H, J=9.2 Hz, Ph), 7.31 (d, 1H, Ph), 5.75 (dt, 1H, $J_{4,5}$=15.4 Hz, $J_{5,6a}$=$J_{5,6b}$=7.0 Hz, H-5), 5.48 (dd, 1H, $J_{3,4}$=7.0 Hz, H-4), 4.38 (dd, 1H, $J_{2,3}$=3.6 Hz, H-3), 2.72 (d, 1H, $J_{1a,2}$=4.0 Hz, H-1a), 2.61 (ddd, 1H, $J_{1b,2}$=6.2 Hz, H-2), 2.14 (d, 1H, H-1b), 2.07 (q, 2H, J=7.0 Hz, H-6a, 6b), 1.25 (s, 22H, methylene), 0.89 (s, 9H, t-butyl), 0.88 (t, 1H, J=7.0 Hz, methyl), 0.06 (s, 6H, methyl). Molecular formula: C$_{30}$H$_{51}$N$_3$O$_5$Si [molecular weight (calcd.) 561.844]. Elemental analysis calcd.: C 64.13, H 9.15, N 7.48; found: C 63.87, H 9.20, N 7.10. The properties of compound 7E were as follows.

$[\alpha]_D^{26}$=−28° (C=1.0, CHCl$_3$). $^1$H-NMR (270 MHz, CDCl$_3$); δ: 9.16 (d, 1H, J=2.5 Hz, Ph), 9.12 (d, 1H, $J_{2,NH}$=8.8 Hz, NH), 8.25 (dd, 1H, J=9.5 Hz, Ph), 6.95 (d, 1H, Ph), 5.79 (dt, 1H, $J_{4,5}$=15.7 Hz, $J_{5,6a}$=$J_{5,6b}$=6.6 Hz, H-5), 5.51 (dd, 1H, $J_{3,4}$=7.0 Hz, H-4), 4.47 (dd, 1H, $J_{2,3}$=3.6 Hz, H-3), 4.12 (dt, 1H, $J_{1a,2}$=$J_{1a,OH}$=3.3 Hz, $J_{1gem}$=11.7 Hz, H-1a), 3.83 (dddd, 1H, $J_{1b,2}$=8.0 Hz, H-2), 3.70 (ddd, 1H, $J_{1b,OH}$=4.8 Hz, H-1b), 2.57 (dd, 1H, OH), 2.06 (q, 2H, J=6.6 Hz, H-6a and 6b), 1.26 (s, 22H, methylene), 0.89 (s, 9H, t-butyl), 0.88 (t, 3H, J=7.0 Hz, methyl), 0.02 (s, 6H, methyl). Molecular formula: C$_{30}$H$_{53}$N$_3$O$_6$Si [molecular weight (calcd.) 579.860]. Elemental analysis calcd.: C 62.14, H 9.21, N 7.25; found: C 61.95, H 9.51, N 7.30.

1-4: Synthesis of (2S,3R,4E)-2-[(2,4-dinitrophenyl)amino]-3-(t-butyldimethylsilyloxy)-1-iodo-4-octadecene [compound 8E: in formula (7-8E), R$_3$=I]

Compound 7E (232 mg, 0.400 mmol) was dissolved in 10 ml of toluene. Then 210 mg (0.800 mmol) of triphenylphosphine, 203 mg (0.800 mmol) of iodine and 109 mg (1.60 mmol) of imidazole were added thereto and the resulting mixture was stirred at room temperature for 30 minutes. The product thus obtained was purified by silica gel column chromatography (eluent; ethyl acetate:hexane=1:30). Thus 269 mg of compound 8E was obtained (yield: 97%). The properties of compound 8E were as follows.

$[\alpha]_D^{26}$=−35° (C=0.82, CHCl$_3$). $^1$H-NMR (270 MHz, CDCl$_3$); δ: 9.15 (d, 1H, J=2.6 Hz, Ph), 8.71 (d, 1H, $J_{2,NH}$=9.1 Hz, NH), 8.26 (dd, 1H, J=9.5 Hz, Ph), 6.97 (d, 1H, Ph), 5.79 (dt, 1H, $J_{4,5}$=15.7 Hz, $J_{5,6a}$=$J_{5,6b}$=6.6 Hz, H-5), 5.42 (dd, 1H, $J_{3,4}$=8.0 Hz, H-4), 4.32 (dd, 1H, $J_{2,3}$=5.5 Hz, H-3), 3.72 (dddd, 1H, $J_{1a,2}$=5.1 Hz, $J_{1b,2}$=6.2 Hz, H-2), 3.49 (dd, 1H, $J_{1gem}$=11.0 Hz, H-1a), 3.43 (dd, 1H, H-1b), 2.05–1.97 (m, 2H, H-6a and 6b), 1.25 (s, 22H, methylene), 0.88 (s, 9H, t-butyl), 0.88 (t, 3H, J=6.6 Hz, methyl), 0.07 and 0.04 (2s, each 3H, methyl). Molecular formula: C$_{30}$H$_{52}$IN$_3$O$_5$Si [molecular weight (calcd.) 689.756]. Elemental analysis calcd.: C 52.24, H 7.60, N 6.09; found: C 52.01, H 7.85, N 6.01.

1-5: Synthesis of compound 6E (from compound 8E)

Compound 8E (269 mg, 0.390 mmol) was dissolved in 8 ml of pyridine. Then 64 mg (0.507 mmol) of silver fluoride was added thereto at 0° C. in the dark and the resulting mixture was stirred under the same conditions for 2 hours. The reaction mixture was diluted with ethyl acetate and washed with water. The resulting product was purified by silica gel column chromatography (15 g of K-60 manufactured by Katayama Kagaku, eluent; ethyl acetate:hexane=1:20). Thus 188 mg of compound 6E was obtained (yield: 86%). 1-6: Synthesis of (2S,3R,4E)-1-[(5a-carba-2,3;4,6-di-O-isopropylidene-β-D-xylo-hex-5-enopyranosyl)amino]-2-[(2,4-dinitrophenyl)amino]-3-(t-butyldimethylsilyloxy)-4-octadecene (compound 10E)

Compound 9 represented by the following formula:

(35 mg, 0.139 mmol) and 65 mg (0.116 mmol) of compound 6E were dissolved in 0.5 ml of 2-propanol and heated to 120° C. for 5 days. Then the reaction mixture was concentrated under reduced pressure and the resulting residue was purified by silica gel column chromatography (8 g of K-60 manufactured by Katayama Kagaku, eluent: ethyl acetate:toluene=1:15). Thus 57 mg of compound 10E was obtained (yield: 60%). The properties of compound 10E were as follows.

$[\alpha]_D^{26} = -3°$ (C=1.0, CHCl$_3$). $^1$H-NMR (270 MHz, CDCl$_3$); δ: 9.14 (d, 1H, J=2.9 Hz, Ph), 9.08 (d, 1H, J=7.3 Hz, NH), 8.21 (dd, 1H, J=9.4 Hz, Ph), 7.03 (d, 1H, Ph), 5.72 (dt, 1H, $J_{4,5}$=15.4 Hz, $J_{5,6a}$=$J_{5,6b}$=7.3 Hz, H-5), 5.44 (dd, 1H, $J_{3,4}$=6.8 Hz, H-4), 5.30 (bs, 1H, H-5'a), 4.62 (d, 1H, $J_{3',4'}$=7.8 Hz, H-4'), 4.49 and 4.14 (2d, each 1H, $J_{6'gem}$=14.2 Hz, H-6'a and 6'b), 4.33 (dd, 1H, $J_{2,3}$=4.4 Hz, H-3), 3.88–3.78 (m, 1H, H-2), 3.71 (dd, 1H, $J_{2',3'}$=9.0 Hz, H-3'), 3.57 (bd, 1H, $J_{1',2'}$=9.0 Hz, H-1'), 3.45 (t, 1H, H-2'), 3.16 (dd, 1H, $J_{1a,2}$=4.9 Hz, $J_{1gem}$=12.7 Hz, H-1a), 3.03 (dd, 1H, $J_{1b,2}$=4.4 Hz, H-1b), 2.07–1.98 (m, 2H, H-6a and 6b), 1.57, 1.44, 1.42 and 1.40 (4s, each 3H, methyl), 1.25 (s, 22H, methylene), 0.88 (t, 3H, J=7.0 Hz, methyl), 0.86 (s, 9H, t-butyl), −0.02 and −0.05 (2s, each 3H, methyl). Molecular formula: C$_{43}$H$_{72}$N$_4$O$_9$Si [molecular weight (calcd.) 817.162]. Elemental analysis calcd.: C 63.20, H 8.88, N 6.86; found: C 62.85, H 9.15, N 6.72.

1-7: Synthesis of (2S,3R,4E)-1-[(5a-carba-β-D-xylo-hex-5-enopyranosyl)amino]-$^2$-[(2,4-dinitrophenyl)amino]-4-octadecen-3-ol (compound 11E)

Compound 10E (40 mg, 0.0489 mmol) was dissolved in 3 ml of tetrahydrofuran (THF) and 73 μl (0.0730 mmol) of a 1M solution of tetrabutylammonium fluoride (nBu$_4$NF) in THF was added thereto. Then the resulting mixture was stirred at room temperature for 15 minutes. The reaction mixture was diluted with ethyl acetate and washed with water. Then the organic layer was dried over Glauber's salt and concentrated under reduced pressure. The resulting residue was dissolved in 1.6 ml of acetic acid and 0.4 ml of water and stirred at 70° C. for 30 minutes. The reaction mixture was concentrated under reduced pressure and the resulting product was purified by silica gel column chromatography (1 g of K-60 manufactured by Katayama Kagaku, eluent; ethanol:toluene=1:7). Thus 23 mg of compound 11E was obtained (yield: 75%). The properties of compound 11E were as follows.

$[\alpha]_D^{27} = -50°$ (C=1.2, MeOH). $^1$H-NMR (270 MHz, CDCl$_3$+CD$_3$OD, 2:1); δ: 9.11 (d, 1H, J=2.5 Hz, Ph), 8.25 (dd, 1H, J=9.5 Hz, Ph), 7.14 (d, 1H, Ph), 5.81 (dt, 1H, $J_{4,5}$=15.4 Hz, $J_{5,6a}$=$J_{5,6b}$=6.7 Hz, H-5), 5.58 (bs, 1H, H-5'a), 5.49 (dd, 1H, $J_{3,4}$=7.0 Hz, H-4), 4.31–4.06 (m, 4H, H-3,4', 6a' and 6'b), 3.85 (q, 1H, $J_{1a,2}$=$J_{1b,2}$=$J_{2,3}$=6.0 Hz, H-2), 3.54 (dd, 1H, $J_{2',3'}$=9.9 Hz, $J_{3',4'}$=8.0 Hz, H-3'), 3.45 (dd, 1H, $J_{1',2'}$=8.0 Hz, H-2'), 3.27 (bd, 1H, H-1'), 3.18 (dd, 1H, $J_{1gem}$=12.5 Hz, H-1a), 2.87 (dd, 1H, H-1b), 2.06–2.00 (m, 2H, H-6a and 6b), 1.26 (s, 22H, methylene), 0.88 (t, 3H, J=7.0 Hz, methyl). Molecular formula: C$_{31}$H$_{50}$N$_4$O$_9$ [molecular weight (calcd.) 622.769]. Elemental analysis calcd.: C 59.79, H 8.09, N 9.00; found: C 59.41, H 8.42, N 8.63.

1-8: Synthesis of (2S,3R,4E)-1-[(5a-carba-β-D-xylo-hex-5-enopyranosyl)amino]-2-(hexadecanoylamino)-4-octadecen-3-ol (compound 1E)

Compound 11E (23 mg, 0.0369 mmol) was dissolved in 2 ml of a mixture of acetone, methanol and water (3:5:2) and 0.5 ml of a basic resin Amberlite IRA-400(OH$^-$) was added thereto at room temperature. After stirring for 2 hours, the reaction mixture was filtered through a Celite filter and the filtrate was concentrated under reduced pressure. The resulting residue was dissolved in 2 ml of THF. Then 11 μl (0.0369 mmol) of palmitoyl chloride and 1 ml of a 30% aqueous solution of sodium acetate were added thereto at room temperature and the mixture was stirred for 15 minutes. The reaction mixture was diluted with 20 ml of THF and washed with 10 ml of a saturated aqueous solution of sodium chloride. Then the organic layer was dried over anhydrous magnesium sulfate and concentrated under reduced pressure. The resulting residue was dissolved in 1.8 ml of n-butanol and 0.2 ml of a 1M aqueous solution of potassium hydroxide was added thereto. After stirring the reaction mixture at 50° C. for 18 hours, the resulting product was purified by silica gel column chromatography (2 g of K-60 manufactured by Katayama Kagaku, eluent; methanol:chloroform=1:7). Thus 15 mg of compound 1E was obtained (yield: 58%). The properties of compound 1E were as follows.

$[\alpha]_D^{27} = -21°$ (C=0.35, MeOH). $^1$H-NMR (270 MHz, CDCl$_3$+CD$_3$OD, 2:1); δ: 5.73 (dt, 1H, $J_{4,5}$=15.3 Hz, $J_{5,6a}$=$J_{5,6b}$=6.4 Hz, H-5), 5.58 (bs, 1H, H-5'a), 5.44 (dd, 1H, $J_{3,4}$=6.9 Hz, H-4), 4.25–4.10 (m, 3H, H-4',6a' and 6'b), 4.08 (dd, 1H, $J_{2,3}$=5.9 Hz, H-3), 3.89 (q, 1H, $J_{1a,2}$=$J_{1b,2}$=5.9 Hz, H-2), 3.55 (dd, 1H, $J_{2',3'}$=9.9 Hz, $J_{3',4'}$=7.4 Hz, H-3'), 3.43 (dd, 1H, $J_{1',2'}$=8.4 Hz, H-2'), 3.27 (bd, 1H, H-1'), 2.98 and 2.81 (2dd, each 1H, $J_{1gem}$=12.6 Hz, H-1a and 1b), 2.20 (t, 2H, J=7.5 Hz, COCH$_2$), 2.04 (q, 1H, J=6.5 Hz, H-6a and 6b), 1.27 (s, 48H, methylene), 0.89 (t, 6H, J=6.5 Hz, methyl). Molecular formula: C$_{41}$H$_{78}$N$_2$O$_6$ [molecular weight (calcd.) 695.089]. Elemental analysis calcd.: C 70.85, H 11.31, N 4.03; found: C 70.34, H 11.75, N 3.88.

EXAMPLE 2

Synthesis of (2S,3R,4Z)-1-[(5a-carba-β-D-xylo-hex-5-enopyranosyl)amino]-2-(hexadecanoylamino)-4-octadecen-3-ol (compound 1Z)

2-1: Synthesis of (2S,3R,4Z)-2-azido-1-benzoyloxy-4-octadecen-3-ol [compound 4Z; in formula (3-5Z), R$_1$=benzoyl(Bz)oxy, R$_2$=H]

(2S,3R,4Z)-2-azido-1,3-dihydroxy-4-octadecene [compound 3Z; in the formula (3-5Z), R$_1$=R$_2$=H] (1.76 g, 5.41 mmol) was treated in the same manner as in the synthesis of compound 4E. Thus 1.65 g of compound 4Z was obtained (yield: 71%). The properties of this compound 4Z were as follows.

$[\alpha]_D^{24} = -28°$ (C=1.1, CHCl$_3$). $^1$H-NMR (270 MHz, CDCl$_3$). δ: 8.07–8.04 (m, 2H, Ph), 7.58–7.42 (m, 3H, Ph), 5.59 (dt, 1H, $J_{4,5}$=11.0 Hz, $J_{5,6a}$=$J_{5,6b}$=7.3 Hz, H-5), 5.43 (dd, 1H, $J_{3,4}$=8.8 Hz, H-4), 4.65 (dd, 1H, $J_{2,3}$=5.2 Hz, H-3), 4.52 (dd, 1H, $J_{1a,2}$=4.0 Hz, $J_{1gem}$=11.7 Hz, H-1a), 4.31 (dd, 1H, $J_{1b,2}$=2.1 Hz, H-1b), 3.69 (ddd, 1H, H-2), 2.15–2.10 (m,

2H, H-6a, 6b), 1.25 (s, 22H, methylene), 0.88 (t, 3H, J=7.0 Hz, methyl). Molecular formula: $C_{25}H_{39}N_3O_3$ [molecular weight (calcd.) 429.608]. Elemental analysis calcd.: C 69.90, H 9.15, N 9.78; found: C 69.72, H 9.40, N 9.61.

2-2: Synthesis of (2S,3R,4Z)-2-azido-3-(t-butyldimethylsilyloxy)-4-octadecen-1-ol [compound 5Z; in formula (3-5Z), $R_1$=H, $R_2$=t-BDMS]

Compound 4Z (1.65 g, 3.84 mmol) was treated in the same manner as in the synthesis of compound 5E. Thus 2.03 mg of compound 5Z was obtained (yield: 84%). The properties of compound 5Z were as follows.

$[\alpha]_D^{26}$=−40° (C=1.0, $CHCl_3$). $^1$H-NMR (270 MHz, $CDCl_3$). δ: 5.55 (dt, 1H, $J_{4,5}$=11.0 Hz, $J_{5,6a}$=$J_{5,6b}$=7.3 Hz, H-5), 5.40 (dd, 1H, $J_{3,4}$=8.8 Hz, H-4), 4.59 (dd, 1H, $J_{2,3}$=5.5 Hz, H-3), 3.77 (dd, 1H, $J_{1a,2}$=5.1 Hz, $J_{1gem}$=11.0 Hz, H-1a), 3.69 (dd, 1H, $J_{1b,2}$=5.1 Hz, H-1b), 3.37 (dt, 1H, H-2), 2.18 (t, 1H, J=6.0 Hz, OH), 2.10–2.00 (m, 2H, H-6a, 6b), 1.25 (s, 22H, methylene), 0.88 (s, 9H, t-butyl), 0.89 (t, 3H, J=7.0 Hz, methyl), 0.09 and 0.05 (2s, each 3H, methyl). Molecular formula: $C_{24}H_{49}N_3O_2Si$ [molecular weight (calcd.) 439.762]. Elemental analysis calcd.: C-65.56, H 11.23, N 9.56; found: C 65.35, H 11.63, N 9.61.

2-3: Synthesis of (2S,3R,4Z)-3-(t-butyldimethylsilyloxy)-1,2-[(2,4-dinitrophenyl)imino]-4-octadecene (compound 6Z) and (2S,3R,4Z)-2-[(2,4-dinitrophenyl)amino]-3-(t-butyldimethylsilyloxy)-4-octadecen-1-ol [compound 7Z; in formula (7-8Z), $R_3$=OH]

Compound 5Z (1.01 g, 2.30 mmol) was treated in the same manner as in the synthesis of compound 6E. Thus 537 mg of compound 6Z (yield: 42%) and 431 mg of compound 7Z (yield: 33%) were obtained. The properties of compound 6z were as follows.

$[\alpha]_D^{25}$=−140° (C=0.93, $CHCl_3$). $^1$H-NMR (270 MHz, $CDCl_3$). δ: 8.85 (d, 1H, J=2.4 Hz, Ph), 8.27 (dd, 1H, J=9.3 Hz, Ph), 7.33 (d, 1H, Ph), 5.57 (dt, 1H, $J_{4,5}$=10.7 Hz, $J_{5,6a}$=$J_{5,6b}$=7.3 Hz, H-5) 5.40 (dd, 1H, $J_{3,4}$=8.3 Hz, H-4), 4.78 (dd, 1H, $J_{2,3}$=3.4 Hz, H-3), 2.72 (d, 1H, $J_{1a,2}$=3.4 Hz, H-1a), 2.61 (dt, 1H, $J_{1b,2}$=5.9 Hz, H-2), 2.15 (d, 1H, H-1b), 2.15–2.00 (m, 2H, H-6a, 6b), 1.24 (s, 22H, methylene), 0.89 (s, 9H, t-butyl), 0.88 (t, 3H, J=7.0 Hz, methyl), 0.063 and 0.056 (2s, each 3H, methyl). Molecular formula: $C_{30}H_{51}N_3O_5Si$ [molecular weight (calcd.) 561.844]. Elemental analysis calcd.: C 64.13, H 9.15, N 7.48; found: C 63.78, H 9.51, N 7.21.

The properties of compound 7Z were as follows.

$[\alpha]_D^{25}$=−18° (C=0.95, $CHCl_3$). $^1$H-NMR (270 MHz, $CDCl_3$). δ: 9.17 (d, 1H, $J_{2,NH}$=8.4 Hz, NH), 9.16 (d, 1H, J=2.6 Hz, Ph), 8.24 (dd, 1H, J=9.9 Hz, Ph), 6.96 (d, 1H, Ph), 5.57 (dt, 1H, $J_{4,5}$=11.3 Hz, $J_{5,6a}$=$J_{5,6b}$=7.3 Hz, H-5), 5.49 (dd, 1H, $J_{3,4}$=8.1 Hz, H-4), 4.81 (dd, 1H, $J_{2,3}$=4.0 Hz, H-3), 4.14 (dt, 1H, $J_{1a,2}$=J1a,OH=3.3 Hz, $J_{1gem}$=11.5 Hz, H-1a), 3.86 (ddd, 1H, $J_{1b,2}$=4.0 Hz, $J_{1b,OH}$=8.4 Hz, H-1b), 3.67 (ddt, 1H, H-2), 2.57 (dd, 1H, OH), 2.17–1.96 (m, 2H, H-6a and 6b), 1.26 (s, 22H, methylene), 0.89 (s, 9H, t-butyl), 0.88 (t, 3H, J=7.0 Hz, methyl), 0.03 (s, 6H, methyl). Molecular formula: $C_{30}H_{53}N_3O_6Si$ [molecular weight (calcd.) 579.860]. Elemental analysis calcd.: C 62.14, H 9.21, N 7.25; found: C 62.20, H 9.31, N 7.41.

2-4: Synthesis of (2S,3R,4Z)-2-[(2,4-dinitrophenyl)amino]-3-(t-butyldimethylsilyloxy)-1-iodo-4-octadecene [compound 8Z; in formula (7-8Z), $R_3$=I]

Compound 7Z (158 mg, 0.272 mmol) was treated in the same manner as in the synthesis of compound 8E. Thus 172 mg of compound 8Z was obtained (yield: 91%). The properties of compound 8Z were as follows.

$[\alpha]_D^{26}$=−30° (C=0.75, $CHCl_3$). $^1$H-NMR (270 MHz, $CDCl_3$). δ: 9.15 (d, 1H, J=2.5 Hz, Ph), 8.77 (d, 1H, $J_{2,NH}$=9.5 Hz, NH), 8.24 (dd, 1H, J=9.5 Hz, Ph), 6.98 (d, 1H, Ph), 5.55 (dt, 1H, $J_{4,5}$=11.0 Hz, $J_{5,6a}$=$J_{5,6b}$=6.7 Hz, H-5), 5.36 (dd, 1H, $J_{3,4}$=8.8 Hz, H-4), 4.64 (dd, 1H, $J_{2,3}$=5.9 Hz, H-3), 3.70 (ddt, 1H, $J_{1a,2}$=$J_{1b,2}$=5.1 Hz, H-2), 5.52 (d, 2H, H-1a and 1b), 2.17–1.96 (m, 2H, H-6a and 6b), 1.26 (s, 22H, methylene), 0.89 (s, 9H, t-butyl), 0.88 (t, 1H, J=6.9 Hz, methyl), 0.09 and 0.05 (2s, each 3H, methyl). Molecular formula: $C_{30}H_{52}IN_3O_5Si$ [molecular weight (calcd.) 689.756]. Elemental analysis calcd.: C 52.24, H 7.60, N 6.09; found: C 51.89, H 7.95, N 5.78.

2-5: Synthesis of compound 6Z from compound 8Z

Compound 8Z (172 mg, 0.249 mmol) was treated in the same manner as in the synthesis of compound 6E from compound 8E. Thus 126 mg of compound 6Z was obtained (yield: 90%). 2-6: Synthesis of (2S,3R,4Z)-1-[(5a-carba-2,3;4,6-di-O-isopropylidene-β-D-xylo-hex-5-enopyranosyl) amino-2-[(2,4-dinitrophenyl)amino]-3-(t-butyldimethylsilyloxy)-4-octadecene (compound 10Z)

(the part corresponding to that in compound 10E is omitted.)

Compound 9 (51 mg, 0.200 mmol) and compound 6Z (89 mg, 0.158 mmol) were treated in the same manner as in the synthesis of compound 10E. Thus 65 mg of compound 10Z was obtained (yield: 50%). The properties of compound 10Z were as follows.

$[\alpha]_D^{27}$=−13° (C=0.72, $CHCl_3$). $^1$H-NMR (270 MHz, $CDCl_3$). δ: 9.15 (d, 1H, $J_{2,NH}$=9.5 Hz, NH), 9.14 (d, 1H, J=2.9 Hz, Ph), 8.19 (dd, 1H, J=9.9 Hz, Ph), 7.03 (d, 1H, Ph), 5.51 (dt, 1H, $J_{4,5}$=11.0 Hz, $J_{5,6a}$=$J_{5,6b}$=7.0 Hz, H-5), 5.41 (dd, 1H, $J_{3,4}$=8.1 Hz, H-4), 5.29 (bs, 1H, H-5'a), 4.65 (dd, 1H, $J_{2,3}$=4.4 Hz, H-3), 4.62 (bd, 1H, $J_{3,4}$=8.1 Hz, H-4'), 4.49 and 4.14 (2bd, each 1H, $J_{6gem}$=13.5 Hz, H-6'a and 6'b), 3.81 (ddt, 1H, $J_{1a,2}$=5.5 Hz, $J_{1b,2}$=4.4 Hz, H-2), 3.70 (dd, 1H, $J_{2',3'}$=9.5 Hz, H-3'), 3.55 (bd, 1H, $J_{1',2'}$=8.4 Hz, H-1'), 3.44 (dd, 1H, H-2'), 3.19 (dd, 1H, $J_{1gem}$=12.8 Hz, H-1a), 3.04 (dd, 1H, H-1b), 2.12–1.94 (m, 2H, H-6a and 6b), 1.56, 1.43, 1.42 and 1.40 (4s, each 3H, methyl), 1.26 (s, 22H, methyl), 0.88 (t, 3H, J=6.6 Hz, methyl), 0.87 (s, 9H, t-butyl), −0.01 and −0.02 (2s, each 3H, methyl). Molecular formula: $C_{43}H_{72}N_4O_9Si$ [molecular weight (calcd.) 817.162]. Elemental analysis calcd.: C 63.20, H 8.88, N 6.86; found: C 62.91, H 9.10, N 7.01.

2-7: Synthesis of (2S,3R,4Z)-1-[(5a-carba-β-D-xylo-hex-5-enopyranosyl)amino-2-[(2,4-dinitrophenyl)amino]-4-octadecen-3-ol (compound 11Z)

(the part corresponding to that in compound 11E is omitted.)

Compound 10Z (51 mg, 0.0624 mmol) was treated in the same manner as in the synthesis of compound 11E. Thus 36 mg of compound 11Z was obtained (yield: 93%). The properties of compound 11Z were as follows.

$[\alpha]_D^{26}=-83°$ (C=0.93, MeOH). $^1$H-NMR (270 MHz, CDCl$_3$+CD$_3$OD, 2:1). δ: 9.10 (d, 1H, J=2.5 Hz, Ph), 8.24 (dd, 1H, J=9.9 Hz, Ph), 7.14 (d, 1H, Ph), 5.59 (s, 1H, H-5'a), 5.58 (dt, 1H, $J_{4,5}$=11.0 Hz, $J_{5,6a}$=$J_{5,6b}$=7.0 Hz, H-5), 5.45 (dd, 1H, $J_{3,4}$=8.4 Hz, H-4), 4.64 (dd, 1H, $J_{2,3}$=6.6 Hz, H-3), 4.30–4.05 (m, 3H, H-4', 6'a and 6'b), 3.88 (ddd, 1H, $J_{1a,2}$=4.4 Hz, $J_{1b,2}$=5.1 Hz, H-2), 3.54 (t, 1H, $J_{2',3'}$=$J_{3',4'}$=9.9 Hz, H-3'), 3.48 (t, 1H, $J_{1,2}$=9.9 Hz, H-2'), 3.82 (bd, 1H, H-1'), 3.24 (dd, 1H, $J_{1gem}$=12.6 Hz, H-1a), 2.93 (dd, 1H, H-1b), 2.18–1.95 (m, 2H, H-6a and 6b), 1.26 (s, 22H, methylene), 0.88 (t, 3H, J=6.6 Hz, methyl). Molecular formula: C$_{31}$H$_{50}$N$_4$O$_9$ [molecular weight (calcd.) 622.769]. Elemental analysis calcd.: C 59.79, H 8.09, N 9.00; found: C 59.38, H 8.45, N 8.70.

2-8: Synthesis of (2S,3R,4Z)-1-[(5a-carba-β-D-xylo-hex-5-enopyranosyl)amino-2-(hexadecanoylamino)-4-octadecen-3-ol (compound 1Z)

Compound 11Z (19 mg, 0.0305 mmol) was treated in the same manner as in the synthesis of compound 1E. Thus 12 mg of compound 1Z was obtained (yield: 57%). The properties of compound 1Z were as follows.

$[\alpha]_D^{26}=-38°$ (C=0.29, MeOH). $^1$H-NMR (270 MHz, CDCl$_3$-CD$_3$OD, 2:1). δ: 5.59 (bs, 1H, H-5'a), 5.57 (dt, 1H, $J_{4,5}$=11.0 Hz, $J_{5,6a}$=$J_{5,6b}$=7.3 Hz, H-5), 5.39 (dd, 1H, $J_{3,4}$= 8.4 Hz, H-4), 4.45 (dd, 1H, $J_{2,3}$=6.6 Hz, H-3), 4.18 and 4.12 (2d, each 1H, $J_{6'gem}$=14.3 Hz, H-6'a and 6'b), 4.20–4.10 (m, 1H, H-4'), 3.91 (dt, 1H, $J_{1a,2}$=6.6 Hz, $J_{1b,2}$=5.1 Hz, H-2), 3.55 (dd, 1H, $J_{2',3'}$=9.9 Hz, $J_{3,4'}$=7.0 Hz, H-3'), 3.47 (dd, 1H, $J_{1',2'}$=8.1 Hz, H-2'), 3.38 (bd, 1H, H-1'), 3.05 (dd, 1H, $J_{1gem}$=12.8 Hz, H-1a), 2.88 (dd, 1H, H-1b), 2.20 (t, 2H, J=7.0 Hz, H-1a" and 1b"), 2.15–2.00 (m, 2H, H-6a and 6b), 1.67–1.52 (m, 2H, H-2"a and 2"b), 1.26 (s, 46H, methylene), 0.89 (t, 6H, J=7.0 Hz, methyl). Molecular formula: C$_{41}$H$_{78}$N$_2$O$_6$·H$_2$O [molecular weight (calcd.) 713.1]. Elemental analysis calcd.: C 69.06, H 11.32, N 3.93; found: C 68.84, H 11.64, N 3.62.

EXAMPLE 3

Synthesis of (2S,3R,4E)-1-[(5a-carba-β-L-arabino-hex-5-enopyranosyl)amino]-2-(hexadecanoylamino)-4-octadecen-3-ol (compound 2E)

3-1: Synthesis of 1-azido-4,6-O-benzylidene-5a-carba-1-deoxy-2,3-di-O-methoxymethyl-β-D-xylo-hex-5-enopyranose (compound 13)

1-Azido-5a-carba-1-deoxy-2,3;4,6-di-O-isopropylidene-β-D-xylo-hex-5-enopyranose (compound 12):

(103 mg, 0.366 mmol) was dissolved in 3 ml of 80% aqueous acetic acid and stirred at 70° C. for 40 hours. Then the reaction mixture was concentrated under reduced pressure and the resulting residue was dissolved in 4 ml of N,N-dimethylformamide (DMF). After adding 137 μl (0.915 mmol) of α,α-dimethoxytoluene and 14 mg (0.0732 mmol) of p-toluenesulfonic acid monohydrate, the resulting mixture was stirred at 55° C. under reduced pressure (<50 mmHg) with the use of an aspirator for 2 hours. The reaction mixture was diluted with ethyl acetate, washed successively with a saturated aqueous solution of sodium bicarbonate and water and then dried over Glauber's salt. The organic layer was concentrated under reduced pressure and the residue was dissolved in 5 ml of methylene chloride. After adding 111 μl (1.46 mmol) of chloromethyl methyl ether and 510 μl (2.93 mmol) of diisopropylethylamine, the mixture was heated under reflux for 12 hours. The resulting product was separated and purified by silica gel column chromatography (10 g of K-60, manufactured by Katayama Kagaku, eluent; ethyl acetate:hexane=1:8). Thus 73 mg of compound 13 was obtained (yield: 53%). The properties of compound 13 were as follows.

$[\alpha]_D^{23}=-120°$ (C=1.2, CHCl$_3$). $^1$H-NMR (270 MHz, CDCl$_3$). δ: 5.65 (s, 1H, PhCH=), 5.51 (bs, 1H, H-5a), 4.99 and 4.81 (2d, each 1H, J=6.6 Hz, methylene), 4.89 and 4.83 (2d, each 1H, J=6.3 Hz, methylene), 4.53 (bd, 1H, $J_{3,4}$=7.7 Hz, H-4), 4.47 (bs, 2H, H-6a and H-6b), 4.08 (bd, 1H, $J_{1,2}$=8.4 Hz, H-1), 3.98 (dd, 1H, $J_{2,3}$=10.6 Hz, H-3), 3.67 (dd, 1H, H-2), 3.64 and 3.51 (2s, each 3H, methyl). Molecular formula: C$_{18}$H$_{23}$N$_3$O$_6$ [molecular weight (calcd.) 377.403]. Elemental analysis calcd.: C 57.29, H 6.14, N 11.13; found: C 56.97, H 6.39, N 10.88.

3-2: Synthesis of 1-azido-6-O-(t-butyldimethylsilyl)-5a-carba-1-deoxy-2,3-di-O-methoxymethyl-β-D-xylo-hex-5-enopyranose (compound 14) [in formula (14-15), R$^4$=H]

Compound 13 (269 mg, 0.713 mmol) was dissolved in 6 ml of 80% aqueous acetic acid and stirred at 60° C. for 1 hour. Then the reaction mixture was concentrated under reduced pressure and the thus obtained residue was dissolved in 6 ml of DMF. After adding 216 mg (1.43 mmol) of t-butyldimethylchlorosilane and 194 mg (2.85 mmol) of imidazole, the mixture was stirred at room temperature for 1 hour. Then the reaction mixture was diluted with ethyl acetate and washed with water. The resulting product was purified by silica gel column chromatography (20 g of K-60, manufactured by Katayama Kagaku, eluent; ethyl acetate:toluene=1:10). Thus 211 mg of compound 14 was obtained (yield: 73%). The properties of this compound 14 were as follows.

$[\alpha]_D^{25}=-109°$ (C=0.90, CHCl$_3$). $^1$H-NMR (270 MHz, CDCl$_3$). δ: 5.64 (bs, 1H, H-5a), 4.90, 4.82, 4.78 and 4.77 (4d, each 1H, J=6.7 Hz, methylene), 4.33 and 4.23 (2bd, each 1H, $J_{6gem}$=13.6 Hz, H-6a and H-6b), 4.22–4.16 (m, 1H,

H-4), 4.10 (d, 1H, $J_{4,OH}$=2.6 Hz, OH). 4.00 (bd, 1H, $J_{1,2}$=8.0 Hz, H-1), 3.68 (dd, 1H, $J_{2,3}$=9.9 Hz, H-2), 3.54 (dd, 1H, $J_{3,4}$=7.0 Hz, H-3), 3.48 and 3.47 (2s, each 3H, methyl), 0.92 (s, 9H, t-butyl), 0.09 (s, 6H, methyl). Molecular formula: $C_{17}H_{33}N_3O_6Si$ [molecular weight (calcd.) 403.557]. Elemental analysis calcd.: C 50.60, H 8.24, N 10.41; found: C 50.25, H 8.42, N 10.31.

3-3: Synthesis of 4-O-acetyl-1-azido-6-O-(t-butyldimethylsilyl)-5a-carba-1-deoxy-2,3-di-O-methoxymethyl-β-D-xylo-hex-5-enopyranose (compound 15) [in formula (14-15), $R^5$=acetyl (Ac)]

Compound 14 (6.0 mg, 0.0149 mmol) was acetylated by treating with pyridine and acetic anhydride overnight at room temperature. After isolating the product, 8.0 mg of compound 15 was obtained (yield: 100%). The properties of compound 15 were as follows.

$[\alpha]_D^{25}$=−32° (C=0.40, CHCl$_3$). $^1$H-NMR (270 MHz, CDCl$_3$). δ: 5.78 (bs, 1H, H-5a), 5.61 (bd, 1H, $J_{3,4}$=7.3 Hz, H-4), 4.90, 4.80, 4.78 and 4.70 (4d, each 1H, J=6.6 Hz, methylene), 4.06–3.97 (m, 3H, H-1, 6a and 6b), 3.82 (dd, 1H, $J_{2,3}$=9.5 Hz, H-3), 3.72 (dd, 1H, $J_{1,2}$=7.4 Hz, H-2), 3.48 and 3.35 (2s, each 3H, methyl), 2.10 (s, 3H, acetyl), 0.90 (s, 9H, t-butyl), 0.06 (s, 6H, methyl). Molecular formula: $C_{19}H_{35}N_3O_7Si$ [molecular weight (calcd.) 445.595]. Elemental analysis calcd.: C 51.21, H 7.92, N 9.43; found: C 50.90, H 8.21, N 9.51.

3-4: Synthesis of 1-azido-6-O-(t-butyldimethylsilyl)-5a-carba-1-deoxy-2,3-di-O-methoxymethyl-α-L-arabino-hex-5-enopyranose (compound 16) [in formula (16-17), $R^5$=H, $R^6$=azide]

(16~17)

Compound 14 (223 mg, 0.553 mmol) was dissolved in 5 ml of methylene chloride. In the presence of 220 mg of a molecular sieves 4Å powder, 358 mg (1.66 mmol) of pyridinium chlorochromate (PCC) was added thereto and the resulting mixture was stirred at room temperature for 1.5 hours. Then the product was purified by silica gel column chromatography (ether). The ketone thus obtained was dissolved in 6 ml of toluene. A 1M solution of diisopropyl aluminum hydride (DIBAL-H) in toluene (0.737 mmol, 1.11 mmol) was added thereto at −78° C. and the mixture was stirred for 20 minutes. After adding a 5% aqueous solution of sodium hydroxide, the reaction mixture was extracted with ethyl acetate and washed with a saturated aqueous solution of sodium chloride. Then the organic layer was dried over Glauber's salt. The resulting residue was separated and purified by silica gel column chromatography (10 g of K-60, manufactured by Katayama Kagaku, eluent; ethyl acetate:toluene=1:8). Thus 119 mg of compound 16 (yield: 53%) and 71 mg of compound 14 (yield: 32%) were obtained. The properties of compound 16 were as follows.

$[\alpha]_D^{23}$=−107° (C=1.3, CHCl$_3$). $^1$H-NMR (270 MHz, CDCl$_3$). δ: 5.70 (bs, 1H, H-5a), 4.89, 4.85, 4.79 and 4.78 (4d, each 1H, J=6.6 Hz, methylene), 4.30–4.27 (m, 2H, H-4 and 6a), 4.20 (bd, 1H, $J_{6gem}$=13.6 Hz, H-6b), 4.00 (dd, 1H, $J_{1a,2}$=7.7 Hz, $J_{2,3}$=9.9 Hz, H-2), 3.86 (bd, 1H, H-1), 3.67 (dd, 1H, $J_{3,4}$=3.8 Hz, H-3), 3.48 and 3.44 (2s, each 3H, methyl), 2.75 (d, 1H, $J_{4,OH}$=2.6 Hz, OH), 0.92 (s, 9H, t-butyl), 0.10 (s, 6H, methyl). Molecular formula: $C_{17}H_{33}N_3O_6Si$ [molecular weight (calcd.) 403.557]. Elemental analysis calcd.: C 50.60, H 8.24, N 10.41; found: C 50.31, H 8.51, N 10.15.

3-5: Synthesis of 4-O-acetyl-1-azido-6-O-(t-butyldimethylsilyl)-5a-carba-1-deoxy-2,3-di-O-methoxymethyl-α-L-arabino-hex-5-enopyranose (compound 17) [in formula (16-17), $R^5$=acetyl, $R^6$=azide]

Compound 16 (35 mg, 0.0867 mmol) was acetylated in the same manner as the one described above. Thus 34 mg of compound 17 was obtained (yield: 89%). The properties of compound 17 were as follows.

$[\alpha]_D^{25}$=−23° (C=1.1, CHCl$_3$). $^1$H-NMR (270 MHz, CDCl$_3$). δ: 5.85 (bs, 1H, H-5a), 5.57 (d, 1H, $J_{3,4}$=3.7 Hz, H-4), 4.94, 4.77, 4.73 and 4.63 (4d, each 1H, J=6.8 Hz, methylene), 4.08–4.06 (m, 2H, H-6a and 6b), 3.97 (dd, 1H, $J_{1,2}$=7.7 Hz, $J_{2,3}$=9.9 Hz, H-2), 3.89 (d, 1H, H-1), 3.79 (dd, 1H, H-3), 3.50 and 3.38 (2s, each 3H, methyl), 2.09 (s, 3H, acetyl), 0.91 (s, 9H, t-butyl), 0.06 (s, 6H, methyl). Molecular formula: $C_{19}H_{35}N_3O_7Si$ [molecular weight (calcd.) 445.595]. Elemental analysis calcd.: C 51.21, H 7.92, N 9.43; found: C 51.02, H 8.25, N 9.69.

3-6: Synthesis of (2S,3R,4E)-1-[6-O-t-butyldimethylsilyl-5a-carba-2,3-di-O-methoxymethyl-α-L-arabino-hex-5-enopyranosyl)-amino]-2-(2,4-dinitrophenyl)amino]-3-(t-butyldimethylsilyloxy)-4-octadecene (compound 18E)

Compound 16 (66 mg, 0.165 mmol) was dissolved in 3 ml of THF and 51 mg (0.196 mmol) of triphenylphosphine and 150 μl of water were added thereto. After stirring at 60° C. for 5 hours, the reaction mixture was concentrated under reduced pressure. Then the resulting residue was subjected to silica gel column chromatography (2 g of K-60 manufactured by Katayama Kagaku, eluent; ethanol:toluene=1:8) to thereby remove triphenylphosphine oxide. Thus an amine 16a of the formula (16-17), wherein $R^5$ was a hydrogen atom and $R^6$ was an amino group, was obtained. This product and 125 mg (0.222 mmol) of compound 6E obtained in Example 1 were dissolved in 2-propanol and heated to 120° C. for 5 days in a sealed tube. Then the reaction mixture was concentrated under reduced pressure and the resulting residue was separated and purified by silica gel column chromatography (10 g of K-60, manufactured by Katayama Kagaku, eluent; ethyl acetate:toluene=1:8). Thus 82 mg of compound 18E was obtained (yield: 55%). The properties of compound 18E were as follows.

$[\alpha]_D^{26}$=−30° (C=1.1, CHCl$_3$). $^1$H-NMR (270 MHz, CDCl$_3$). δ: 9.30 (d, 1H, $J_{2,NH}$=8.8 Hz, NH), 9.15 (d, 1H, J=2.4 Hz, Ph), 8.21 (dd, 1H, J=9.8 Hz, Ph), 7.01 (d, 1H, Ph), 5.73 (dt, 1H, $J_{4,5}$=15.6 Hz, $J_{5,6a}$=$J_{5,6b}$=6.9 Hz, H-5), 5.66 (d, 1H, $J_{1',5'a}$=1.8 Hz, H-5'a), 5.48 (dd, 1H, $J_{3,4}$=6.8 Hz, H-4), 4.86, 4.83, 4.77 and 4.75 (4d, each 1H, J=6.8 Hz, methylene), 4.36 (dd, 1H, $J_{2,3}$=3.3 Hz, H-3), 4.28 (d, 1H, $J_{3',4'}$=3.9 Hz, H-4'), 4.22 and 4.14 (2bd, each 1H, $J_{6'gem}$=13.2 Hz, H-6'a and 6'b), 3.92 (dd, 1H, $J_{1,2}$=8.0 Hz, $J_{2,3}$=10.0 Hz, H-2'), 3.76 (ddt, 1H, $J_{1a,2}$=$J_{1b,2}$=4.9 Hz, H-2), 3.61 (dd, 1H, H-3'), 3.43 and 3.39 (2s, each 3H, methyl), 3.15 and 2.69 (2dd, each 1H, $J_{1gem}$=12.7 Hz, H-1a and 1b), 2.05–2.00 (m, 2H, H-6a and 6b), 1.26 (s, 22H, methylene), 0.88 (t, 3H, J=7.3 Hz, methyl), 0.86 and 0.84 (2s, each 9H, t-butyl), 0.05, 0.04, −0.05 and −0.07 (4s, each 3H, methyl). Molecular formula: $C_{47}H_{76}N_4O_{11}Si_2$ [molecular weight (calcd.) 929.323]. Elemental analysis calcd.: C 60.74, H 8.24, N 6.03; found: C 60.42, H 8.61, N 6.25.

3-7: Synthesis of (2S,3R,4E)-1-[(5a-carba-α-L-arabino-hex-5-enopyranosyl)-amino]-2-(2,4-dinitrophenyl)amino]-4-octadecen-3-ol (compound 19E)

Compound 18E (23 mg, 0.0245 mmol) was dissolved in 2 ml of THF and 60 μl (0.060 mmol) of a 1M solution of nBu$_4$NF in THF was added thereto at room temperature. After stirring for 30 minutes, the reaction mixture was diluted with ethyl acetate and washed with water. The organic layer was dried over Glauber's salt and concentrated under reduced pressure. Then the resulting residue was dissolved in 2.3 ml of THF and 100 μl of 12M hydrochloric acid was added thereto. The reaction mixture was stirred at room temperature for 1 hour and then neutralized with sodium hydrogencarbonate. After concentration, the residue was dissolved in ethanol-chloroform (1:5) and the salt was filtered off. The resulting product was purified by silica gel column chromatography (2 g of K-60 manufactured by Katayama Kagaku, eluent; methanol:chloroform=1:5). Thus 15 mg of compound 19E was obtained (yield: 99%). The properties of compound 19E were as follows.

$[α]_D^{26}$=+31° (C=0.75, MeOH). $^1$H-NMR (270 MHz, CDCl$_3$+CD$_3$OD, 2:1). δ: 9.10 (d, 1H, J=3.1 Hz, Ph), 8.47 (d, 1H, J$_{2,NH}$=7.9 Hz, NH), 8.27 (dd, 1H, J=9.8 Hz, Ph), 7.13 (d, 1H, Ph), 5.86 (dt, 1H, J$_{4,5}$=15.5 Hz, J$_{5,6a}$=J$_{5,6b}$=6.7 Hz, H-5), 5.69 (d, 1H, J$_{1',5'a}$=1.8 Hz, H-5'a), 5.47 (dd, 1H, J$_{3,4}$=7.6 Hz, H-3), 4.69 and 4.52 (2d, each 1H, J$_{7gem}$=10.1 Hz, H-6'a and 6'b), 4.22 (d, 1H, J$_{3',4'}$=4.3 Hz, H-4'), 4.97 (t, 1H, J$_{2,3}$=7.6 Hz, H-3), 3.90 (dd, 1H, J$_{1',2'}$=8.5 Hz, J$_{2',3'}$=10.4 Hz, H-2'), 3.78 (dddd, 1H, J$_{1a,2}$=3.7 Hz, J$_{1b,2}$=10.4 Hz, H-2), 3.52 (dd, 1H, H-3'), 3.49 (dd, 1H, J$_{1gem}$=13.4 Hz, H-1a), 3.48 (dd, 1H, H-1'), 2.92 (dd, 1H, H-1b), 2.07–1.90 (m, 2H, H-6a and 6b), 1.26 (s, 22H, methylene), 0.88 (t, 3H, J=6.5 Hz, methyl). Molecular formula: C$_{31}$H$_{50}$N$_4$O$_9$ [molecular weight (calcd.) 622.769]. Elemental analysis calcd.: C 59.79, H 8.09, N 9.00; found: C 59.61, H 8.25, N 8.79.

3-8: Synthesis of (2S,3R,4E)-1-[(5a-carba-α-L-arabino-hex-5-enopyranosyl)amino]-2-(hexadecanoylamino)-4-octadecen-3-ol (compound 2E)

Compound 19E (15 mg, 0.0241 mmol) was treated in the same manner as in the synthesis of compound 1E. Thus 8.2 mg of compound 2E was obtained (yield: 49%). The properties of compound 2E were as follows.

$[α]_D^{24}$=+12° (C=0.25, MeOH). $^1$H-NMR (270 MHz, CDCl$_3$+CD$_3$OD, 2:1). δ: 5.73 (dt, 1H, J$_{4,5}$=15.4 Hz, J$_{5,6a}$= J$_{5,6b}$=6.6 Hz, H-5), 5.68 (d, 1H, J$_{1',5'a}$=1.7 Hz, H-5'a), 5.44 (dd, 1H, J$_{3,4}$=6.6 Hz, H-4), 4.18 (d, 1H, J$_{3',4'}$=4.4 Hz, H-4'), 4.15 (s, 2H, H-6a and 6b), 4.08 (dd, 1H, J$_{2,3}$=5.8 Hz, H-3), 3.89 (q, 1H, J$_{1a,2}$=J$_{1b,2}$=5.8 Hz, H-2), 3.65 (dd, 1H, J$_{1',2'}$=8.0 Hz, J$_{2',3'}$=9.5 Hz, H-2'), 3.48 (dd, 1H, H-3'), 3.13 (dd, 1H, H-1'), 3.00 and 2.79 (2dd, each 1H, J$_{1gem}$=12.4 Hz, H-1a and 1b), 2.19 (t, 2H, J=6.6 Hz, H-1"a and 1"b), 2.04 (q, 1H, J=6.6 Hz, H-6a and 6b), 1.27 (s, 48H, methylene), 0.86 (t, 6H, J=7.3 Hz, methyl). Molecular formula: C$_{41}$H$_{78}$N$_2$O$_6$ [molecular weight (calcd. ) 695.089]. Elemental analysis calcd.: C 70.85, H 11.31, N 4.03; found: C 70.55, H 11.72, N 3.72.

EXAMPLE 4
Synthesis of (2S,3R,4Z)-1-[(5a-carba-α-L-arabino-hex-5-enopyranosyl )amino]-2-(hexadecanoylamino)-4-octadecen-3-ol (compound 2Z)

4-1: Synthesis of (2S,3R,4Z)-1-[(6-O-t-butyldimethylsilyl-5a-carba-2,3-di-O-methoxymethyl-α-L-arabino-hex-5-enopyranosyl)-amino]-2-[(2,4-dinitrophenyl)amino]-3-(t-butyldimethylsilyloxy)-4-octadecene (compound 18Z)

(the part corresponding to that in compound 18E is omitted.)

Compound 16a (52 mg, 0.129 mmol) synthesized in Example 3 (3-6) and 88 mg (0.157 mmol) of compound 6Z described in Example 2 (2-3) were treated in the same manner as in the synthesis of compound 18E. Thus 46 mg of compound 18Z was obtained (yield: 41%). The properties of compound 18Z were as follows.

$[α]_D^{23}$=−18° (C=1.2, CHCl$_3$). $^1$H-NMR (270 MHz, CDCl$_3$). δ: 9.41 (d, 1H, J$_{2,NH}$=8.8 Hz, NH), 9.16 (d, 1H, J=2.6 Hz, Ph), 8.21 (dd, 1H, J=9.9 Hz, Ph), 6.99 (d, 1H, Ph), 5.66 (d, 1H, J$_{1',5'a}$=2.2 Hz, H-5'a), 5.50 (dt, 1H, J$_{4,5}$=11.4 Hz, J$_{5,6a}$=J$_{5,6b}$=5.7 Hz, H-5), 5.44 (dd, 1H, J$_{3,4}$=7.1 Hz, H-4), 4.86, 4.82, 4.77 and 4.74 (4d, each 1H, J=6.6 Hz, methylene), 4.68 (dd, 1H, J$_{2,3}$=3.8 Hz, H-3), 4.28 (d, 1H, J$_{3',4'}$=3.7 Hz, H-4'), 4.22 and 4.14 (2bd, each 1H, J$_{6gem}$=13.1 Hz, H-6'a and 6'b), 3.92 (dd, 1H, J$_{1',2'}$=7.9 Hz, J$_{2',3'}$9.7 Hz, H-2), 3.71 (ddt, 1H, J$_{1a,2}$=J$_{1b,2}$=4.6 Hz, H-2), 3.62 (dd, 1H, H-3'), 3.43 and 3.38 (2s, each 3H, methyl), 3.36 (dd, 1H, H-1'), 3.22 and 2.72 (2dd, each 1H, J$_{1gem}$=12.6 Hz, H-1a and 1b), 2.15–1.95 (m, 2H, H-6a and 6b), 1.26 (s, 22H, methyl), 0.88 (t, 3H, J=7.3 Hz, methyl), 0.86 and 0.84 (2s, each 9H, t-butyl), 0.05, 0.04, −0.06 and −0.07 (4s, each 3H, methyl). Molecular formula: C$_{47}$H$_{76}$N$_4$O$_{11}$Si$_2$ [molecular weight (calcd.) 929.323]. Elemental analysis calcd.: C 60.74, H 8.24, N 6.03; found: C 60.39, H 8.16, N 5.79.

4-2: Synthesis of (2S,3R,4Z)-1-[(5a-carba-α-L-arabino-hex-5-enopyranosyl)amino]-2-[(2,4-dinitrophenyl)amino]-4-octadecen-3-ol (compound 19Z)

(the part corresponding to that in compound 19E is omitted.)

Compound 18Z (23 mg, 0.0245 mmol) was treated in the same manner as in the synthesis of compound 19E. Thus 14 mg of compound 19Z was obtained (yield: 92%). The properties of compound 19Z were as follows.

$[α]_D^{25}$=−86° (C=0.76, MeOH). $^1$H-NMR (270 MHz, CDCl$_3$+CD$_3$OD, 2:1). δ: 9.10 (d, 1H, J=2.6 Hz, Ph), 8.48 (d, 1H, J$_{2,NH}$=9.5 Hz, NH), 8.26 (dd, 1H, J=9.4 Hz, Ph), 7.15 (d, 1H, Ph), 5.70 (s, 1H, H-5'a), 5.67 (dt, 1H, J$_{4,5}$=11.2 Hz, J$_{5,6a}$=J$_{5,6}$b=7.7 Hz, H-5), 5.43 (dd, 1H, J$_{2,3}$=8.6 Hz, H-4), 4.69 and 4.53 (2d, each 1H, J$_{6'gem}$=10.2 Hz, H-6'a and 6'b), 4.35 (t, 1H, J$_{2,3}$=8.6 Hz, H-3), 4.23 (d, 1H, J$_{3',4'}$=3.4 Hz, H-4'), 3.89 (dd, 1H, $J_{1',2'}$=8.5 Hz, $J_{2'},{3'}$=10.3 Hz, H-2'), 3.82 (dddd, 1H, $J_{1a,2}$=5.1 Hz, $J_{1b,2}$=10.3 Hz, H-2), 3.52 (dd, 1H, H-3'), 3.48 (dd, 1H, $J_{1gem}$=12.8 Hz, H-1a), 3.38 (bd, 1H, H-1'), 2.95 (dd, 1H, H-1b), 2.20–2.00 (m, 2H, H-6a and 6b), 1.26 (s, 22H, methylene), 0.89 (t, 3H, J=6.4 Hz, methyl). Molecular formula: $C_{31}H_{50}N_4O_9 \cdot H_2O$ [molecular weight (calcd.) 640.785]. Elemental analysis calcd.: C 58.11, H 8.18, N 8.74; found: C 58.45, H 8.50, N 8.35.

4-3: Synthesis of (2S,3R,4Z)-1-[(5a-carba-α-L-arabino-hex-5-enopyranosyl)amino]-2-(hexadecanoylamino)-4-octadecen-3-ol (compound 2Z)

Compound 19Z (15 mg, 0.0241 mmol) was treated in the same manner as in the synthesis of compound 1E. Thus 9.2 mg of compound 2Z was obtained (yield: 59%).

$[\alpha]_D^{26}$=−7° (C=0.36, MeOH). $^1$H-NMR (270 MHz, CDCl$_3$+CD$_3$OD, 2:1). δ: 5.70 (d, 1H, $J_{1',5'a}$=1.0 Hz, H-5'a), 5.56 (dt, 1H, $J_{4,5}$=11.1 Hz, $J_{5,6a}$=$J_{5,6b}$=7.5 Hz, H-5), 5.39 (dd, 1H, $J_{3,4}$=8.2 Hz, H-4), 4.45 (dd, 1H, $J_{2,3}$=6.0 Hz, H-3), 4.18 (dd, 1H, $J_{3',4'}$=4.3 Hz, H-4'), 4.18 and 4.13 (2d, each 1H, $J_{6'gem}$=13.8 Hz, H-6'a and 6'b), 3.90 (dt, 1H, $J_{1a,2}$=6.0 Hz, $J_{1b,2}$=5.1 Hz, H-2), 3.66 (dd, 1H, $J_{1,2}$=8.5 Hz, $J_{2',3'}$=10.2 Hz, H-2'), 3.48 (dd, 1H, H-3'), 3.16 (dd, 1H, H-1'), 3.04 (dd, 1H, $J_{1gem}$=12.0 Hz, H-1a), 2.83 (dd, 1H, H-1b), 2.20 (t, 1H, J=7.7 Hz, H-1"a and 1"b), 2.20–1.98 (m, 2H, H-6a and 6b), 1.26 (s, 48H, methylene), 0.88 (t, 6H, J=7.0 Hz, methyl). Molecular formula: $C_{41}H_{78}N_2O_6 \cdot H_2O$ [molecular weight (calcd.) 713.105]. Elemental analysis calcd.: C 69.06, H 11.31, N 3.93; found: C 69.07, H 11.62, N 3.89.

Test Example 1

Glycosidase inhibitory effects of glycolipid analogs (1) The inhibitory effects of each of compounds 1E, 1Z, 2E and 2Z synthesized in Examples 1 to 4 on β-glucocerebrosidase and β-galactocerebrosidase were determined by using fluorescence-labeled natural substrates, i.e., 12-[N-methyl-N-(7-nitro-2-oxa-1,3-diaxol-4-yl)]aminododecanoic acid (NBD)-glucocerebroside and NBD-galactocrebroside. Namely, the β-glucocerebrosidease activity was determined in accordance with the method of Granbowski et al. [Clin. Chim. Acta., 1241, 123–135 (1982)] with the use of mouse liver microsome as an enzyme source. On the other hand, the β-galactocerebrosidase activity was determined in accordance with the method of Raghavan et al. [Biochim. Biophys. Acta, 877, 1–8 (1986)] with the use of mouse brain microsome as an enzyme source. Table 1 shows the results. Each substrate was used in a constant and large excess amount over the corresponding enzyme. Compounds 1E and 1Z, each having an unsaturated sugar analog of glucose type in the pseudo-cerebroside, strongly and specifically inhibited the β-glucocerebrosidase activity alone at a concentration of 10 µM. IC$_{50}$ levels (the concentration necessary for inhibiting 50% of the enzyme activity) of compounds 1E and 1Z were 0.3 µM and 0.1 µM, respectively. On the other hand, compounds 2E and 2Z, each having an unsaturated sugar analog of galactose type in the pseudo-cerebroside, strongly and specifically inhibited the β-galactocerebrosidase activity alone at a concentration of 10 µM. IC$_{50}$ levels of compounds 2E and 2Z were 1.6 µM and 2.3 µM, respectively. The inhibition (%) was determined in accordance with the following formula.

Inhibition (%) =

$$\frac{(1 - \text{enzyme activity in the presence of inhibitor})}{(\text{enzyme activity in the absence of inhibitor})} \times 100.$$

Under the same conditions as employed above, further, the inhibitory effects of the following compound C-1 [in the formula (a), X=NH, sugar analog=glucose type] being similar to the glycolipid analogs of the present invention and the sugar analogs C-2 to C-4 represented by the following formula [synthesized by the method similar to in the synthesis of compound C-1] were examined and compared. Table 1 shows the results.

TABLE 1

Inhibitory effects of pseudo-cerebrosides on β-glucocerebrosidase and β-galactocerebrosidase

| | β-Glucocerebrosidase | | β-galactocerebrosidase | |
|---|---|---|---|---|
| Compound | 10 µM inhibition (%) | IC$_{50}$ (µM) | 10 µM inhibition (%) | IC$_{50}$ (µM) |
| 1E | 95.2 | 0.3 | 0 | — |
| 2E | 0 | — | 92.6 | 1.6 |
| 1Z | 97.7 | 0.1 | 0 | — |
| 2Z | 0 | — | 87.2 | 2.3 |
| C-1 | 37.3 | — | 0 | — |
| C-2 | 0 | — | 12.9 | — |
| C-3 | 64.0 | — | 2.3 | — |
| C-4 | 0 | — | 15.4 | — |

—: not determined.

As Table 1 shows, the unsaturated glycolipid analogs 1E and 1Z of glucose type according to the present invention each almost completely inhibited the β-glucocerebrosidase activity. The inhibitory activities of these compounds were extremely enhanced, compared with the comparative compounds C-1 and C-3 which were saturated glycolipid analogs of glucose type.

On the other hand, the unsaturated glycolipid analogs 2E and 2Z of galactose type according to the present invention each strongly and specifically inhibited the β-galactocerebrosidase activity.

In contrast, the comparative compounds C-2 and C-4 which were saturated glycolipid analogs of galactose type slightly inhibited the β-galactocerebrosidase activity.

These results indicate that the effectiveness of the unsaturated glycolipid analogs of the present invention in imitating the transition state of an enzyme reaction. (2) The inhibitory effects of each of compounds 1E, 1Z, 2E and 2Z synthesized in Examples 1 to 4, the above-described compound C-1 and the following compounds C-5 and C-6 on β-glucocerebrosidase and β-galactocerebrosidase were determined by the following method. Namely, the same enzyme sources as employed in the above (1) were used, while 4-methyl-umbelliferyl glucoside was used as a substrate. The inhibition (%) and $IC_{50}$ were determined in accordance with the method of Peter et al. [Clin. Chim. Acta, 60, 391–396 (1975)]. In each case, the substrate was used in a constant and large excess amount over the corresponding enzyme.

Table 2 shows the results.

TABLE 2

Inhibitory effects of pseudo-cerebrosides on β-glucocerebrosidase and β-galactocerebrosidase

| Compound | β-Glucocerebrosidase | | β-galactocerebrosidase | |
|---|---|---|---|---|
| | 40 μM inhibition (%) | $IC_{50}$ (μM) | 40 μM inhibition (%) | $IC_{50}$ (μM) |
| 1E | 97 | 0.580 | 1 | — |
| 2E | 31 | — | 95 | 1.25 |
| 1Z | 99 | 0.440 | 1 | — |
| 2Z | 43 | — | 92 | 1.85 |
| C-1 | 56 | — | 7 | — |
| C-5 | 0 | — | 31 | — |
| C-6 | 0 | — | 0 | — |

—: not determined.

As Table 2 shows, the glycolipid analogs of the present invention were highly effective, compared with the comparative compounds, similar to the case of (1) even though the substrate was altered.

That is to say, Tables 1 and 2 indicate that the enzyme inhibitory activity can be largely enhanced, compared with one having a similar structure, by converting the structure of the sugar analog moiety of a pseudo-cerebroside into an unsaturated structure according to the present invention.

Test Example 2
Inhibitory effect of glycolipid analogs on HIV production (neutralization assay of HIV-1 in vitro)

Figure 1:
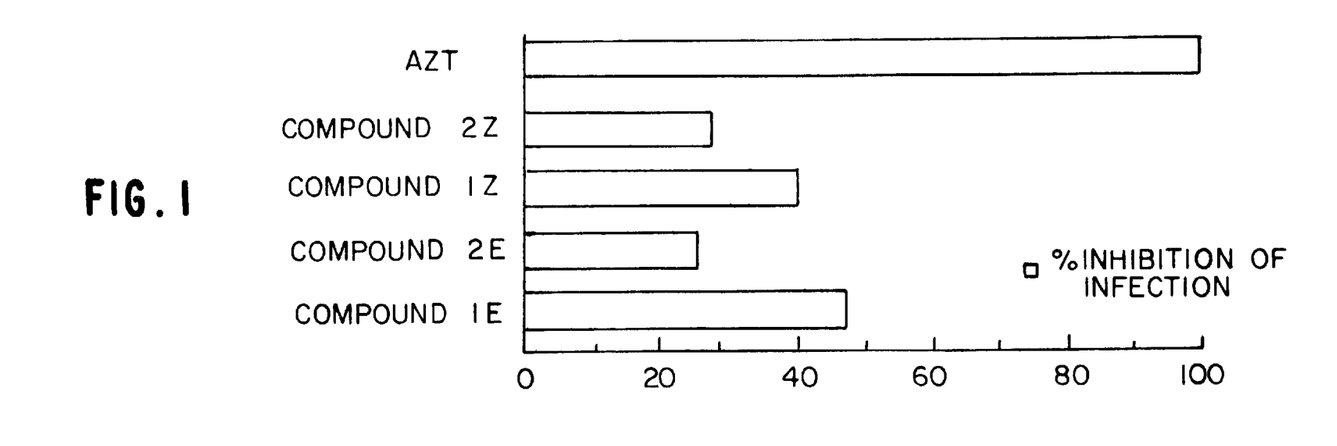
FIG. 1 shows the effects of the glycolipid analogs of the present invention on HIV production by PHA-activated PBMC newly infected with HIV.

The in vitro neutralizing activity in the compounds of the present invention were determined by PBMC-based virus neutralization assay. The test compounds were incubated with 100 TCID50 units of $HIV_{MN}$ (H9/HTLV-III$_{MN}$, AIDS Research and Reference Reagent Program, NIH, Rockville, Md.) for 60 minutes at 37° C. The mixture was transferred to eppendorf tube containing 1×10$^6$ of normal human peripheral blood mononuclear cells (PBMC) activated with 5 μg of PHA for 24 hours and shook for 60 minutes in 37° C. water bath. After washing 3 times with PBS, the cells were suspended with 1 ml of RPMI 1640 medium containing 10% heat-inactivated FCS supplemented with penicillin (50 units/ml), streptomycin (50 mg/ml), and L-glutamine (2 mM) in the presence of recombinant human IL-2 (40 units/ml. Shionogi Pharm. Co., Osaka, Japan) and cultured in culture tube (A-S Nunc, Roskilde, Denmark) for 7 days. The supernatant generation of HIV was measured by HIV-1 p24 antigen ELISA (Dinabot, LTD., Tokyo, Japan) (J. Immunol., 142, 4248–4255 (1989), J. Immunol., 148, 2175–2180 (1992)). The $HIV_{MN}$ stock virus was prepared by incubation of 100 $TCID_{50}$ of $HIV_{MN}$ with normal human PBMC activated with 5 μg/ml of PHA for 7 days followed by 7 days-culture. The cell-free supernatant was stored at −130° C. until use as source of virus. For the neutralization assays, virus stocks were titrated on the PHA-activated normal PBMC and $TCID_{50}$ per ml of each virus was defined. Azidothymidine (AZT) was used as a control. The degree of inhibition of these compounds was expressed as % inhibition taking the inhibition effect of AZT as 100%.

FIG. 1 shows the results. The compounds of the present invention exhibited anti-HIV activity as demonstrated in FIG. 1.

Test Example 3
Inhibitory effects of glycolipid analogs on syncitium formation

Figure 2:
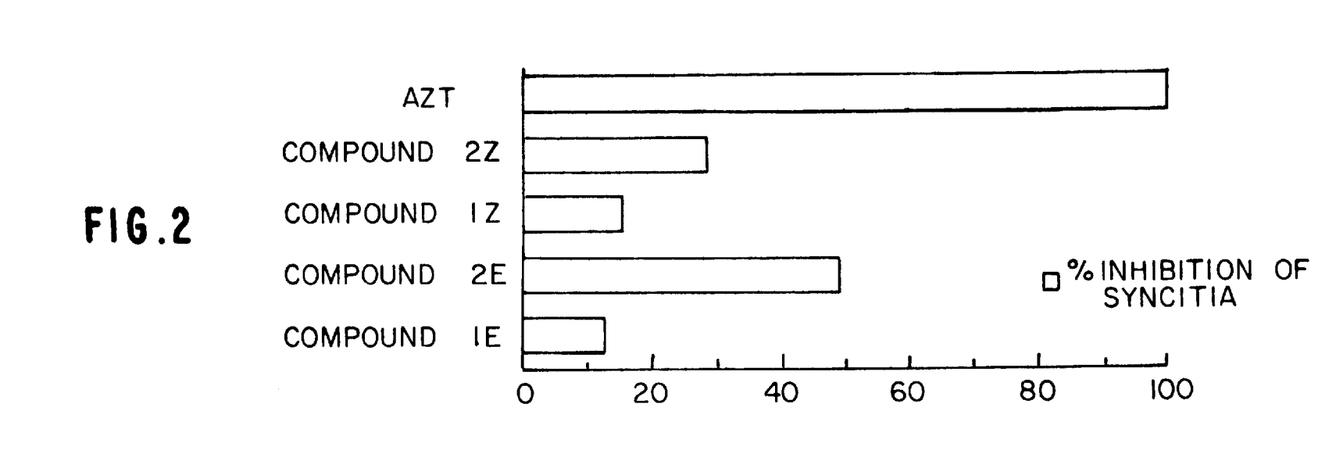
FIG. 2 shows the effects of the glycolipid analogs of the present invention on Syncitium formation of Molt-4/cl8 co-cultured with Molt-4/IIIB.

The inhibition efficacy of the compounds of the present invention on syncitium formation was assessed as follows. A 0.2 ml portion of the culture medium containing 10$^4$ Molt-4/cl8 was transferred into each well of a 96-well flat-bottomed tissue-culture plastic plate, and the cells were allowed to settle at 37° C. After 4 hour, the media were aspirated and replaced with media each containing the respective test compound (10 μM) (FIG. 2). After overnight incubation, the media were aspirated and 10$^4$ Molt-4/IIIB was added to each well. Incubation was continued at 37° C. in 5% $CO_2$. On the fourth day, the cell suspensions from each well were split and seeded into two new wells, and 0.2 ml of fresh medium containing the test compounds was added. This procedure was repeated on the seventh day. Cells were examined by microscopy after day 10. As a control, AZT was used. The degree of inhibition of the test compounds was expressed as % inhibition of syncitia taking the inhibition effect of AZT as 100%.

FIG. 2 shows the results. As shown in FIG. 2, the compounds of the present invention exhibited anti-HIV activity.

The present invention provides glycolipid analogs of novel structure. By regulating and forming the stereostructure of the glycolipid analogs into a desired type, the inhibitory activities on various glycosidases can be controlled. Also, the degree of the inhibitory activity on a particular glycosidase can be controlled thereby. In particular, the glycolipid analogs according to the present invention structure-specifically and strongly inhibits β-glucocerebrosidase and β-galactocerebrosidase activities. Also, it remains stable in an aqueous solution. These characteristics make it highly useful. It has been proved that such glycolipid analogs would never inhibit the activities of glycosyltransferases such as glucocerebroside synthetase or galactocerebroside synthetase. Thus it is an inhibitor having a high specificity, compared with conventionally known β-glucocerebrosidase inhibitors.

In addition, the glycolipid analogs of the present invention can contribute to studies on systems which seemingly affect various biochemical interactions relating to glycosidase inhibition activities. Thus it is applicable to the development of novel drugs, for example, antiviral agents, drugs for improving nervous functions (antidementia drug, etc.), drugs for treating diseases relating to sugar metabolism (diabetes, etc.) and drugs for regulating immune systems (immuno-adjuvant, etc.)

While the invention has been described in detail and with reference to specific embodiments thereof, it will be apparent to one skilled in the art that various changes and modifications can be made therein without departing from the spirit and scope thereof.

What is claimed is:

1. A glycolipid analog represented by the formula (1):

wherein Z represents an imino group, an oxygen atom or a sulfur atom; m is an integer of from 3 to 12; and n is an integer of from 4 to 22.

2. The glycolipid analog as claimed in claim 1, wherein Z represents an imino group and n is an integer of from 4 to 16.

3. The glycolipid analog as claimed in claim 1 which is represented by the formula (1a) or (1b):

wherein Z represents an imino group; X and Y are different from each other and each represents a hydrogen atom or a hydroxyl group; m is an integer of from 3 to 12; and n is an integer of from 4 to 16.

4. The glycolipid analog as claimed in claim 1, which is selected from a group consisting of (2S,3R,4E)-1-[(5a-carba-β-D-xylo-hex-5-enopyranosyl)amino]-2-(hexadecanoylamino)-4-octadecen-3-ol, (2S,3R,4Z)-1-[(5a-carba-β-D-xylo-hex-5-enopyranosyl)amino]-2-(hexadecanoylamino)-4-octadecen-3-ol, (2S,3R,4E)-1-[(5a-carba-α-L-arabino-hex-5-enopyranosyl)amino]-2-(hexadecanoylamino)-4-octadecen-3-ol and (2S,3R,4Z)-1-[(5a-carba-α-L-arabino-hex-5-enopyranosyl)amino]-2-(hexadecanoylamino)-4-octadecen-3-ol.

5. A glycosidase inhibitor which comprises a glycolipid analog as claimed in claim 1 as an active ingredient and a pharmaceutically or biochemically acceptable carrier.

6. The glycosidase inhibitor as claimed in claim 5, which is a glycocerebrosidase inhibitor.

7. The glycosidase inhibitor as claimed in claim 6, which shows at least glucocerebrosidase inhibitory activity or galactocerebrosidase inhibitory activity.

8. The glycosidase inhibitor as claimed in claim 7, which has β-glucocerebrosidase inhibitory activity, and the active ingredient is represented by the formula (1a) or (1b):

wherein Z represents an imino group, an oxygen atom or a sulfur atom; m is an integer of from 3 to 12; n is an integer of from 4 to 22; X represents a hydrogen atom; and Y represents a hydroxyl group.

9. The glycosidase inhibitor as claimed in claim 7, which has β-galactocerebrosidase inhibitory activity, and the active ingredient is represented by the formula (1a) or (1b):

wherein Z represents an imino group, an oxygen atom or a sulfur atom; m is an integer of from 3 to 12; n is an integer of from 4 to 22; X represents a hydroxl group; and Y represents a hydrogen atom.

10. A method of inhibiting glycosidase which comprises applying a composition containing the glycolipid analog of claim 1 as an active ingredient.

* * * * *